(12) United States Patent
Malamas et al.

(10) Patent No.: US 7,563,796 B2
(45) Date of Patent: Jul. 21, 2009

(54) DIPHENYLIMIDAZOPYRIMIDINES AS INHIBITORS OF β-SECRETASE

(75) Inventors: Michael Sotirios Malamas, Jamison, PA (US); James Joseph Erdei, Feasterville, PA (US); Iwan Suwandi Gunawan, Somerset, NJ (US); Pawel Wojciech Nowak, Montvale, NJ (US); Boyd Lynn Harrison, Princeton Junction, NJ (US)

(73) Assignee: Wyeth, Madison, NJ (US)

( * ) Notice: Subject to any disclaimer, the term of this patent is extended or adjusted under 35 U.S.C. 154(b) by 22 days.

(21) Appl. No.: 11/332,732

(22) Filed: Jan. 13, 2006

(65) Prior Publication Data
US 2006/0160828 A1 Jul. 20, 2006

Related U.S. Application Data

(60) Provisional application No. 60/643,805, filed on Jan. 14, 2005.

(51) Int. Cl.
*C07D 487/04* (2006.01)
*A61K 31/519* (2006.01)
*A61P 25/28* (2006.01)

(52) U.S. Cl. .................. 514/259.1; 544/281; 544/230
(58) Field of Classification Search ............... 544/281, 544/230; 514/259.1
See application file for complete search history.

(56) References Cited

U.S. PATENT DOCUMENTS

| | | | |
|---|---|---|---|
| 4,140,793 | A | 2/1979 | Ward |
| 4,225,613 | A | 9/1980 | Ward |
| 6,054,457 | A | 4/2000 | Setoi et al. |
| 6,399,824 | B1 | 6/2002 | Hofmeister et al. |
| 6,656,957 | B1 | 12/2003 | Allgeier et al. |
| 6,689,804 | B2 | 2/2004 | Wu et al. |
| 6,974,829 | B2 | 12/2005 | Tung et al. |
| 7,285,682 | B2 | 10/2007 | Hu |
| 2005/0282825 | A1 | 12/2005 | Malamas et al. |
| 2005/0282826 | A1 | 12/2005 | Malamas et al. |
| 2006/0111370 | A1 | 5/2006 | Zhu et al. |
| 2006/0173049 | A1 | 8/2006 | Malamas et al. |
| 2006/0183790 | A1 | 8/2006 | Cole et al. |
| 2006/0183792 | A1 | 8/2006 | Fobare et al. |
| 2007/0004730 | A1 | 1/2007 | Zhou |
| 2007/0004786 | A1 | 1/2007 | Malamas et al. |
| 2007/0027199 | A1 | 2/2007 | Malamas et al. |
| 2007/0072925 | A1 | 3/2007 | Malamas et al. |
| 2007/0191431 | A1 | 8/2007 | Zhou |
| 2007/0203116 | A1 | 8/2007 | Quagliato et al. |
| 2008/0051390 | A1 | 2/2008 | Malamas et al. |

FOREIGN PATENT DOCUMENTS

| | | |
|---|---|---|
| EP | 0861831 A1 | 9/1998 |
| GB | 2013192 A | 8/1979 |
| WO | WO 97/45417 A1 | 12/1997 |
| WO | WO 98/45267 | 10/1998 |
| WO | WO 01/87829 A1 | 11/2001 |
| WO | WO 03/053938 A1 | 7/2003 |
| WO | WO 03/064396 A1 | 8/2003 |
| WO | WO 03/094854 A2 | 11/2003 |
| WO | WO 2004/058727 A1 | 7/2004 |
| WO | WO 2005/005412 A1 | 1/2005 |
| WO | WO 2005/058311 A1 | 6/2005 |
| WO | WO 2006/009653 A1 | 1/2006 |
| WO | WO 2006/065277 A2 | 6/2006 |
| WO | WO 2007/005404 A1 | 1/2007 |
| WO | WO 2007/016012 A2 | 2/2007 |

OTHER PUBLICATIONS

Allimony, H. A., et al., Indian J. Chem., Sect. B: Org. Chem. Incl., 1999, 38B(4): 445-451.
Abbott et al., Molecular Medicine Today, 1996, vol. 2, p. 106-113.
Fact Sheet Alzheimer's Association, 2006.
Lefrance-Jullien et al., "Design and charaterization of a new cell-permeant inhibitor of the beta-secretase BACE1", British Journal of Pharmacology, 2005, vol. 145, pp. 228-235.
Lyketsos et al., "Position statement of the American Association for Geriatric Psychiatry regarding principles of care for patients with dementia resulting from Alzheimer's Disease", 2006, vol. 14, pp. 561-573.
Alzheimer's Disease, retrieved from internet on Jun. 27, 2007, http://www.mayoclinic.com/health/alzheimers-disease/DA00161/DSECTION-3.
National Institute of Neurological Disorders and Stroke, "Alzheimer's Disease Information Page", retrieved from internet on Jun. 27, 2007, http://www.ninds.nih.gov/disorders/alzheimersdisease/alzheimersdisease.htm.

(Continued)

*Primary Examiner*—James O Wilson
*Assistant Examiner*—Susanna Moore
(74) *Attorney, Agent, or Firm*—Ram W. Sabnis; Scott K. Larsen; David R. Kurlandsky

(57) ABSTRACT

The present invention provides an amino-imidazolone compound of formula I

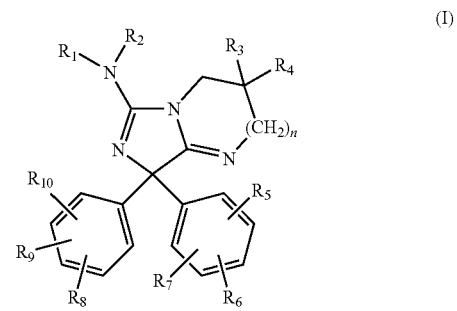

(I)

Also provided are compositions and methods for the use thereof to inhibit β-secretase (BACE) and treat β-amyloid deposits and neurofibrillary tangles.

16 Claims, No Drawings

OTHER PUBLICATIONS

PCT Preliminary Report on Patentability, Written Opinion of the ISR, International Patent Application PCT/US2006/024793, International filing date Jun. 26, 2006.

PCT Preliminary Report on Patentability, Written Opinion of the ISR, International Patent Application PCT/US2006/024912, International filing date Jun. 26, 2006.

Selkoe, "Alzheimer's Disease: Genes, Proteins, and Therapy", Physiological Reviews, 2001, vol. 81(2), pp. 741-766.

Su et al. "Drug delivery across the blood-brain barrier: why is it difficult? How to measure and improve it?", Expert Opinion on Drug Delivery, Abstract, 2006, vol. 3, pp. 419-425.

Tao et al., "Synthesis of Conformationally constrained spirohydantoins with a Dibenzo[a,d]heptadiene ring", Synthesis 2000, No. 10, pp. 1449-1453.

Vandana et al., "Transferring coupled liposomes as drug delivery carriers for brain trageting of 5-florouracil", Journal of Drug Targeting, Abstract, 2005, vol. 13 pp. 245-250.

Varghese et al., "Human beta-secretase (BACE) and BACE Inhibitors", J. Med. Chem. 2003, vol. 46(22), pp. 4625-4630.

Xiao et al., "An improved procedure for the synthesis of 4,4-disubstituted-3-oxo-1,2,5-thiadiazolidine 1,1-dioxides", J. Heterocyclic Chem., 2000, vol. 37, pp. 773-777.

Yamada et al., "Hydantoin derivatives, I. Actions on central nervous system of 5,5-diarylhydantoins and 5,5-diarylhydantion-2-imines", Abstract, Oyo Yakuri, 1975, vol. 9(6), pp. 841-847.

DIPHENYLIMIDAZOPYRIMIDINES AS INHIBITORS OF β-SECRETASE

CROSS-REFERENCE TO RELATED APPLICATIONS

This application claims the benefit under 35 U.S.C. §119 (e) to U.S. Provisional Application No. 60/643,805, filed Jan. 14, 2005, which is hereby incorporated by reference in its entirety.

BACKGROUND OF THE INVENTION

Alzheimer's disease (AD), a progressive degenerative disease of the brain primarily associated with aging, has become a more serious healthcare problem since its initial description almost a century ago (Alzheimer, A. *Centralblatt fur Nervenheikunde und Psychiatrie*, 1907, 30, 117-179). For example, the number of prevalent cases of AD continues to grow at an alarming rate of more than 5% annually in Japan (Citron, M. *J. Neuroscience Research*, 2002, 70, 373-379). Clinically, AD is presented by characterization of loss of memory, cognition, reasoning, judgment, and orientation. Motor, sensory, and linguistic abilities are also affected as the disease progresses until global impairment of multiple cognitive functions occurs. These cognitive losses take place gradually, but typically lead to severe impairment and eventual death in 4-12 years. Consequently, there is an urgent need for pharmaceutical agents capable of halting, preventing or reversing the progression of Alzheimer's disease.

β-Amyloid plaques (predominately an aggregate of a peptide fragment known as Aβ) and neurofibrillary tangles are two major pathologic characterizations associated with Alzheimer's disease. Patients with AD display characteristic β-amyloid deposits (β-amyloid plaques) in the brain and in cerebral blood vessels (β-amyloid angiopathy) as well as neurofibrillary tangles. Amyloidogenic plaques and vascular amyloid angiopathy also characterize the brains of patients with Trisomy 21 (Down's Syndrome), Hereditary Cerebral Hemorrhage with Amyloidosis of the Dutch-type (HCHWA-D), and other neurodegenerative disorders. Neurofibrillary tangles also occur in other dementia-inducing disorders (Varghese, J., et al, Journal of Medicinal Chemistry, 2003, 46, 4625-4630).

β-amyloid deposits are predominately an aggregate of Aβ peptide, which in turn is a product of the proteolysis of amyloid precursor protein (APP). More specifically, Aβ peptide results from the cleavage of APP at the C-terminus by one or more β-secretases, and at the N-terminus by β-secretase enzyme (BACE), also known as aspartyl protease, as part of the β-amyloidogenic pathway.

BACE activity is correlated directly to the generation of Aβ peptide from APP (Sinha, et al., Nature, 1999, 402:537-540), and studies increasingly indicate that the inhibition of BACE inhibits the production of Aβ peptide (Roberds, S. L., et al, Human Molecular Genetics, 2001, 10, 1317-1324).

Thus, based on the foregoing, it is clear that BACE inhibitors are useful, and development of new BACE inhibitors is highly desirable.

SUMMARY OF THE INVENTION

The present invention provides a compound of formula I

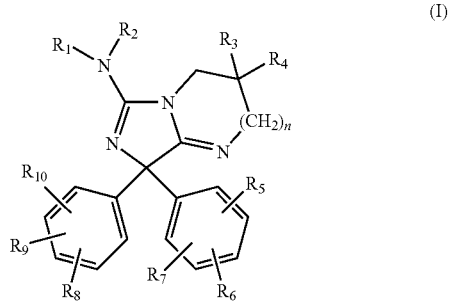

(I)

wherein $R_1$ and $R_2$ are each independently H or an optionally substituted $C_1$-$C_4$ alkyl group;

$R_3$ and $R_4$ are each independently H, or an optionally substituted $C_1$-$C_4$ alkyl group or $R_3$ and $R_4$ may be taken together to form a 4- to 7-membered ring optionally containing one or two heteroatoms selected from O, N or S;

$R_5$, $R_6$ and $R_7$ are each independently H, halogen, $NO_2$, CN, $OR_{11}$, $NR_{12}R_{13}$ or a $C_1$-$C_6$ alkyl, $C_1$-$C_6$ haloalkyl, $C_2$-$C_6$ alkenyl, $C_2$-$C_6$ alkynyl $C_3$-$C_8$ cycloalkyl, cycloheteroalkyl, aryl or aryl($C_1$-$C_4$)alkyl group each optionally substituted or when attached to adjacent carbon atoms $R_5$ and $R_6$ may be taken together with the atoms to which they are attached to form an optionally substituted 5- to 7-membered ring optionally containing one or two heteroatoms selected from O, N or S;

$R_8$, $R_9$ and $R_{10}$ are each independently H, halogen, $NO_2$, CN, $OR_{14}$, $NR_{15}R_{16}$ or a $C_1$-$C_6$ alkyl, $C_1$-$C_6$ haloalkyl, $C_2$-$C_6$ alkenyl, $C_2$-$C_6$ alkynyl, $C_3$-$C_8$ cycloalkyl, cycloheteroalkyl, aryl or aryl($C_1$-$C_4$)alkyl group each optionally substituted or when attached to adjacent carbon atoms $R_8$ and $R_9$ may be taken together with the atoms to which they are attached to form an optionally substituted 5- to 7-membered ring optionally containing one or two heteroatoms selected from O, N or S;

n is 0, 1 or 2;

$R_{11}$ and $R_{14}$ are each independently H or a $C_1$-$C_6$ alkyl, $C_1$-$C_6$ haloalkyl, $C_2$-$C_6$ alkenyl, $C_2$-$C_6$ alkynyl, $C_3$-$C_8$ cycloalkyl or aryl group each optionally substituted; and $R_{12}$, $R_{13}$, $R_{15}$ and $R_{16}$ are each independently H, $C_1$-$C_4$ alkyl, $C_3$-$C_8$ cycloalkyl or $R_{12}$ and $R_{13}$ or $R_{15}$ or $R_{16}$ may be taken together with the atom to which they are attached to form a 5- to 7-membered ring optionally containing an additional heteroatom selected from O, N or S; or a tautomer thereof, a stereoisomer thereof or a pharmaceutically acceptable salt thereof.

The present invention also relates to pharmaceutical compositions and methods for the treatment of β-amyloid deposits and neurofibrillary tangles. Compounds and compositions of the invention are particularly useful in treating Alzheimer's disease, cognitive impairment, Down's Syndrome, HCHWA-D, cognitive decline, senile dementia, cerebral amyloid angiopathy, degenerative dementia, or other neurodegenerative disorders.

DETAILED DESCRIPTION OF THE INVENTION

Alzheimer's disease (AD) is a major degenerative disease of the brain which presents clinically by progressive loss of memory, cognition, reasoning, judgement and emotional stability and gradually leads to profound mental deteoriation and death. The exact cause of AD is unknown, but increasing evidence indicates that amyloid beta peptide (A-beta) plays a central role in the pathogenesis of the disease. (D. B. Schenk; R. E. Rydel et al, Journal of Medicinal Chemistry, 1995, 21,4141 and D. J. Selkoe, Physiology Review, 2001, 81, 741). Patients with AD exhibit characteristic neuropathological markers such as neuritic plaques (and in β-amyloid angiopathy, deposits in cerebral blood vessels) as well as neurofibrillary tangles detected in the brain at autopsy. A-beta is a major component of neuritic plaques in AD brains. In addition, β-amyloid deposits and vascular β-amyloid angiopathy also characterize individuals with Downs Syndrome, Hereditary Cerebral Hemmorhage with Amyloidosis of the Dutch type (HCHWA-D) and other neurodegenreative and dementia-inducing disorders. Over expression of the amyloid precursor protein (APP), altered cleavage of APP to A-beta or a decrease in the clearance of A-beta from a patient's brain may increase the levels of soluble or fibrullar forms of A-beta in the brain. The β-site APP cleaving enzyme, BACE1, also called memapsin-2 or Asp-2, was identified in 1999 (R. Vassar, B. D. Bennett, et al, Nature, 1999, 402, 537). BACE1 is a membrane-bound aspartic protease with all the known functional properties and characteristics of β-secretase. Parallel to BACE1, a second homologous aspartyl protease named BACE2 was found to have β-secretase activity in vitro. Low molecular weight, non-peptide, non-substrate-related inhibitors of BACE1 or β-secretase are earnestly sought both as an aid in the study of the β-secretase enzyme and as potential therapeutic agents.

Surprisingly, it has now been found that amino-imidazolone compounds of formula I demonstrate inhibition of β-secretase and the selective inhibition of BACE1. Advantageously, said amino-imidazolone compounds may be used as effective therapeutic agents for the treatment, prevention or amelioration of a disease or disorder characterized by elevated β-amyloid deposits or β-amyloid levels in a patient. Accordingly, the present invention provides an amino-imidazolone compound of formula I

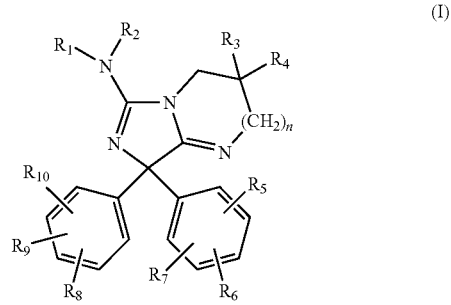

wherein
$R_1$ and $R_2$ are each independently H or an optionally substituted $C_1$-$C_4$alkyl group;
$R_3$ and $R_4$ are each independently H, or an optionally substituted $C_1$-$C_4$ alkyl group or $R_3$ and $R_4$ may be taken together to form a 4- to 7-membered ring optionally containing one or two heteroatoms selected from O, N or S;

$R_5$, $R_6$ and $R_7$ are each independently H, halogen, $NO_2$, CN, $OR_{11}$, $NR_{12}R_{13}$ or a $C_1$-$C_6$alkyl, $C_1$-$C_6$haloalkyl, $C_2$-$C_6$alkenyl, $C_2$-$C_6$alkynyl $C_3$-$C_8$cycloalkyl, cycloheteroalkyl, aryl or aryl($C_1$-$C_4$)alkyl group each optionally substituted or when attached to adjacent carbon atoms $R_5$ and $R_6$ may be taken together with the atoms to which they are attached to form an optionally substituted 5- to 7-membered ring optionally containing one or two heteroatoms selected from O, N or S;

$R_8$, $R_9$ and $R_{10}$ are each independently H, halogen, $NO_2$, CN, $OR_{14}$, $NR_{15}R_{16}$ or a $C_1$-$C_6$alkyl, $C_1$-$C_6$haloalkyl, $C_2$-$C_6$alkenyl, $C_2$-$C_6$alkynyl, $C_3$-$C_8$cycloalkyl, cycloheteroalkyl, aryl or aryl($C_1$-$C_4$)alkyl group each optionally substituted or when attached to adjacent carbon atoms $R_8$ and $R_9$ may be taken together with the atoms to which they are attached to form an optionally substituted 5- to 7-membered ring optionally containing one or two heteroatoms selected from O, N or S;

n is 0, 1 or 2;

$R_{11}$ and $R_{14}$ are each independently H or a $C_1$-$C_6$alkyl, $C_1$-$C_6$haloalkyl, $C_2$-$C_6$alkenyl, $C_2$-$C_6$alkynyl, $C_3$-$C_8$cycloalkyl or aryl group each optionally substituted; and $R_{12}$, $R_{13}$, $R_{15}$ and $R_{16}$ are each independently H, $C_1$-$C_4$alkyl, $C_3$-$C_8$cycloalkyl or $R_{12}$ and $R_{13}$ or $R_{15}$ or $R_{16}$ may be taken together with the atom to which they are attached to form a 5- to 7-membered ring optionally containing an additional heteroatom selected from O, N or S; or a tautomer thereof, a stereoisomer thereof or a pharmaceutically acceptable salt thereof.

As used in the specification and claims, the term halogen designates F, Cl, Br or I and the term cycloheteroalkyl designates a five- to seven-membered cycloalkyl ring system containing 1 or 2 heteroatoms, which may be the same or different, selected from N, O or S and optionally containing one double bond. Exemplary of the cycloheteroalkyl ring systems included in the term as designated herein are the following rings wherein $X_1$ is NR, O or S; and R is H or an optional substituent as described hereinbelow:

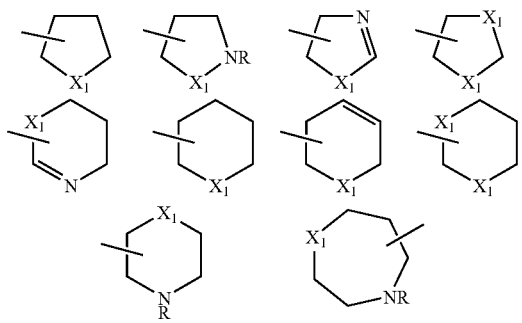

Similarly, as used in the specification and claims, the term aryl designates a carbocyclic aromatic ring system such as phenyl, naphthyl, anthracenyl or the like. The term aryl($C_1$-$C_4$)alkyl designates an aryl group as defined hereinabove attached to a $C_1$-$C_4$alkyl group which may be straight or branched. Said aryl($C_1$-$C_4$)alkyl groups include benzyl, phenethyl, napthtylmethyl, or the like, preferably benzyl. The term haloalkyl as used herein designates a $C_nH_{2n+1}$ group having from one to 2n+1 halogen atoms which may be the same or different and the term haloalkoxy as used herein designates an $OC_nH_{2n+1}$ group having from one to 2n+1 halogen atoms which may be the same or different. Preferably the term haloalkyl designates $CF_3$ and the term haloalkoxy designates $OCF_3$.

In the specification and claims, when the terms $C_1$-$C_6$alkyl, $C_2$-$C_6$alkenyl, $C_2$-$C_6$alkynyl, $C_3$-$C_7$cycloalkyl, cycloheteroalkyl, aryl or aryl($C_1$-$C_4$)alkyl are designated as being optionally substituted, the substituent groups which are optionally present may be one or more of those customarily employed in the development of pharmaceutical compounds or the modification of such compounds to influence their structure/activity, persistence, absorption, stability or other beneficial property. Specific examples of such substituents include halogen atoms, nitro, cyano, thiocyanato, cyanato, hydroxyl, alkyl, haloalkyl, alkoxy, haloalkoxy, amino, alkylamino, dialkylamino, formyl, alkoxycarbonyl, carboxyl, alkanoyl, alkylthio, alkylsuphinyl, alkylsulphonyl, carbamoyl, alkylamido, phenyl, phenoxy, benzyl, benzyloxy, heterocyclyl or cycloalkyl groups, preferably halogen atoms or lower alkyl or lower alkoxy groups. Typically, 0-3 substituents may be present. When any of the foregoing substituents represents or contains an alkyl substituent group, this may be linear or branched and may contain up to 12, preferably up to 6, more preferably up to 4 carbon atoms.

Pharmaceutically acceptable salts may be any acid addition salt formed by a compound of formula I and a pharmaceutically acceptable acid such as phosphoric, sulfuric, hydrochloric, hydrobromic, citric, maleic, malonic, mandelic, succinic, fumaric, acetic, lactic, nitric, sulfonic, p-toluene sulfonic, methane sulfonic acid or the like.

Compounds of the invention include esters, carbamates or other conventional prodrug forms, which in general, are functional derivatives of the compounds of the invention and which are readily converted to the inventive active moiety in vivo. Correspondingly, the method of the invention embraces the treatment of the various conditions described hereinabove with a compound of formula I or with a compound which is not specifically disclosed but which, upon administration, converts to a compound of formula I in vivo. Also included are metabolites of the compounds of the present invention defined as active species produced upon introduction of these compounds into a biological system.

Compounds of the invention may exist as one or more tautomers. One skilled in the art will recognize that compounds of formula I may also exist as the tautomer (It) as shown below.

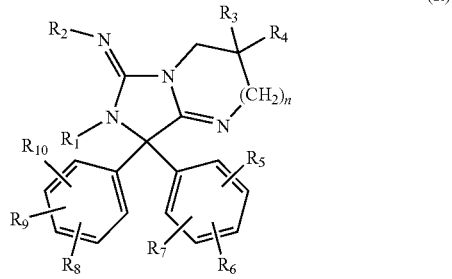

(It)

Tautomers often exist in equilibrium with each other. As these tautomers interconvert under environmental and physiological conditions, they provide the same useful biological effects. The present invention includes mixtures of such tautomers as well as the individual tautomers of Formula I and Formula It.

The compounds of the invention may contain one or more asymmetric carbon atoms or one or more asymmetric (chiral) centers and may thus give rise to optical isomers and diastereomers. Thus, the invention includes such optical isomers and disastereomers; as well as the racemic and resolved, enantiomerically pure stereoisomers; as well as other mixtures of the R and S stereoisomers. One skilled in the art will appreciate that one stereoisomer may be more active or may exhibit beneficial effects when enriched relative to the other stereoisomer(s) or when separated from the other stereoisomer(s). Additionally, the skilled artisan knows how to separate, enrich or selectively prepare said stereoisomers. Accordingly, the present invention comprises compounds of Formula I, the stereoisomers thereof, the tautomers thereof and the pharmaceutically acceptable salts thereof. The compounds of the invention may be present as a mixture of stereoisomers, individual stereoisomers, or as an optically active or enantiomerically pure form. While shown without respect to stereochemistry in Formula I, the present invention includes such optical isomers and diastereomers; as well as the racemic and resolved, enantiomerically pure R and S stereoisomers; as well as other mixtures of the R and S stereoisomers and pharmaceutically acceptable salts thereof. Where a stereoisomer is preferred, it may in some embodiments be provided substantially free of the corresponding enantiomer. Thus, an enantiomer substantially free of the corresponding enantiomer refers to a compound that is isolated or separated via separation techniques or prepared free of the corresponding enantiomer. "Substantially free", as used herein, means that the compound is made up of a significantly greater proportion of one steriosomer, preferably less than about 50%, more preferably less than about 75%, and even more preferably less than about 90%.

Preferred compounds of the invention are those compounds of formula I wherein $R_1$ and $R_2$ are H. Another group of preferred compounds are formula I compounds wherein n is 0 or 1. Also preferred are those compounds of formula I wherein $R_5$ and $R_8$ are each independently a $C_1$-$C_6$alkyl, $C_1$-$C_6$alkoxy, $C_1$-$C_6$haloalkyl or benzyl group each optionally substituted and $R_6$, $R_7$, $R_9$ and $R_{10}$ are H.

More preferred compounds of the invention are those compounds of formula I wherein $R_1$ and $R_2$ are H and n is 0 or 1. Another group of more preferred formula I compounds are those compounds wherein $R_1$, $R_2$, $R_3$ and $R_4$ are H; n is 1; $R_5$ is t-butyl, $CF_3$, $C_1$-$C_3$alkoxy or an optionally substituted benzyl group; $R_8$ is H or $C_1$-$C_3$alkoxy; and $R_9$ is H or $C_1$-$C_3$alkyl.

Preferred compounds of the invention include:
8-(4-tert-butylphenyl)-8-phenyl-2,3,4,8-tetrahydroimidazol[1,5-a]pyrimidin-6-amine;
8-(3-benzylphenyl)-8-phenyl-2,3,4,8-tetrahydroimidazol[1,5-a]pyrimidin-6-amine;
8-[3-(4-fluorophenoxy)phenyl]-8-phenyl-2,3,4,8-tetrahydroimidazo[1,5-a]pyrimidin-6-amine;
8-[3-(4-methoxybenzyl)phenyl]-8-phenyl-2,3,4,8-tetrahydroimidazo[1,5-a]pyrimidin-6-amine;
8-[3-(4-fluorobenzyl)phenyl]-8-phenyl-2,3,4,8-tetrahydroimidazo[1,5-a]pyrimidin-6-amine;
8-phenyl-8-[3-(trifluoromethyl)phenyl]-2,3,4,8-tetrahydroimidazo[1,5-a]pyrimidin-6-amine;
8-(3-methoxyphenyl)-8-phenyl-2,3,4,8-tetrahydroimidazo[1,5-a]pyrimidin-6-amine;
7-(4-methoxy-3-methylphenyl)-7-(3-propoxyphenyl)-2,7-dihydro-3h-imidazo[1,5-a]imidazol-5-amine;
8-(4-methoxy-3-methylphenyl)-8-(3-propoxyphenyl)-2,3,4,8-tetrahydroimidazo[1,5-a]pyrimidin-6-amine;

8-(4-methoxy-3-methylphenyl)-3,3-dimethyl-8-(3-propoxyphenyl)-2,3,4,8-tetrahydroimidazo[1,5-a]pyrimidin-6-amine;

8,8-diphenyl-2,3,4,8-tetrahydroimidazo[1,5-a]pyrimidin-6-amine;

8-[3-(2-cyclopropyl-ethyl)-phenyl]-8-(4-trifluoromethoxy-phenyl)-2,3,4,8-tetrahydro-imidazo[1,5-a]pyrimidin-6-ylamine;

8-(3-allylphenyl)-8-(4-trifluoromethoxyphenyl)-2,3,4,8-tetrahydro-imidazo[1,5-a]pyrimidin-6-ylamine;

8-(3-propyl-phenyl)-8-(4-trifluoromethoxy-phenyl)-2,3,4,8-tetrahydro-imidazo[1,5-a]pyrimidin-6-ylamine;

3-[6-amino-8-(4-trifluoromethoxy-phenyl)-2,3,4,8-tetrahydro-imidazo[1,5-a]pyrimidin-8-yl]-N-ethyl-benzamide;

N-{3-[6-amino-8-(4-trifluoromethoxy-phenyl)-2,3,4,8-tetrahydro-imidazo[1,5-a]pyrimidin-8-yl]-phenyl}-propionamide hydrochloride;

the tautomers thereof, the stereoisomers thereof; or the pharmaceutically acceptable salts thereof.

Compounds of the invention may be readily prepared according to the following reaction scheme, or modification thereof, using readily available starting materials, reagents and conventional synthetic methods. It is also possible to make use of variants of these synthetic methods. For example compounds of formula I wherein $R_1$ and $R_2$ are H (Ia) may be prepared as shown in Scheme I.

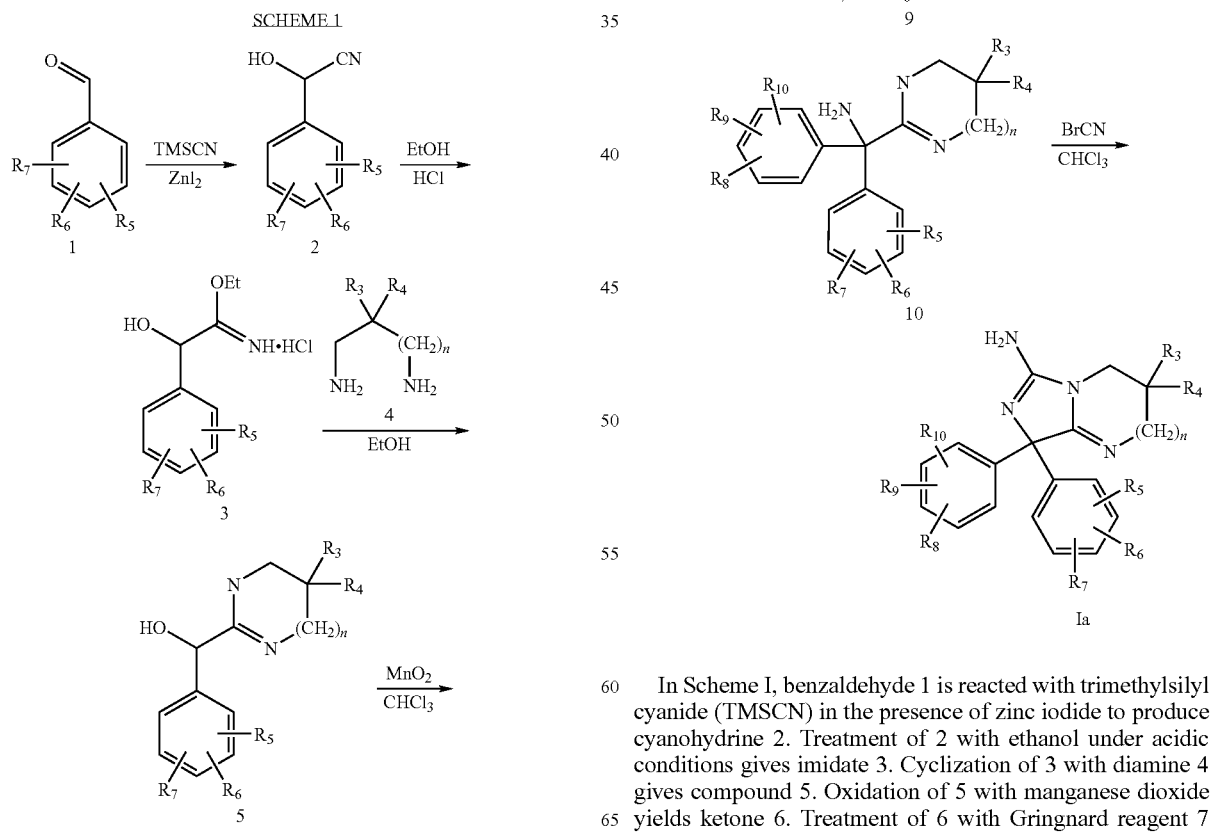

In Scheme I, benzaldehyde 1 is reacted with trimethylsilyl cyanide (TMSCN) in the presence of zinc iodide to produce cyanohydrine 2. Treatment of 2 with ethanol under acidic conditions gives imidate 3. Cyclization of 3 with diamine 4 gives compound 5. Oxidation of 5 with manganese dioxide yields ketone 6. Treatment of 6 with Gringnard reagent 7 affords alcohol 8, which is converted to chloride 9 with thionyl chloride. Chloride 9 is reacted with ammonia to give amine 10. Subsequent treatment of 10 with cyanogen bromide gives the desired compound of formula Ia.

Advantageously, the compounds of the invention are useful for the treatment, prevention or amelioration of a disease or disorder characterized by elevated β-amyloid deposits or β-amyloid levels in a patient, including Alzheimer's disease, Downs Syndrome, Hereditary Cerebral Hemorrhage with Amyloidosis of the Dutch type (HCHWA-D) or other neurodegenerative or dementia-inducing disorders. Accordingly, the present invention also provides methods for the treatment of a disease or disorder associated with excessive BACE activity in a patient in need thereof which comprises providing said patient an effective amount a compound of formula I. Representative diseases include Alzheimer's disease, cognitive impairment, Down's Syndrome, HCHWA-D, cognitive decline, senile dementia, cerebral amyloid angiopathy, degenerative dementia, or other neurodegenerative disorders. Certain of these diseases are characterized by production of β-amyloid deposits or neurofibrillary tangles.

The present invention also provides a method for modulating, preferably inhibiting, the activity of BACE which comprises administering to a patient or contacting a receptor thereof with an effective amount of a compound of formula I.

The present invention also provides a method of ameliorating or preventing β-amyloid deposits in a mammal comprising administering to said mammal an effective amount of a compound of formula I. Further provided is a method for the amelioration or prevention of neurofibrillary tangles in a mammal which comprises administering to said mammal an effective amount of a compound of formula I.

Also provided is a method of ameliorating or preventing Alzheimer's disease, cognitive impairment, Down's Syndrome, HCHWA-D, cognitive decline, senile dementia, cerebral amyloid angiopathy, degenerative dementia, or a neurodegenerative disorder in a mammal comprising administering to said mammal an effective amount of a compound of formula I.

As used in accordance with this invention, the term "providing," with respect to providing a compound or substance covered by this invention, means either directly administering such a compound or substance, or administering a prodrug, derivative, or analog which will form the effective amount of the compound or substance within the body.

The terms "administer", "administering", or "administration", as used herein, refer to either directly administering a compound or composition to a patient, or administering a prodrug derivative or analog of the compound to the patient, which will form an equivalent amount of the active compound or substance within the patient's body.

The term "patient", as used herein, refers to a mammal, preferably a human.

The terms "effective amount", "therapeutically effective amount" and "effective dosage" as used herein, refer to the amount of a compound that, when administered to a patient, is effective to at least partially ameliorate (and, in preferred embodiments, cure) a condition from which the patient is suspected to suffer. The therapeutically effective amount provided in the treatment of a specific disease or disorder may vary according to the specific condition(s) being treated, the size, age and response pattern of the patient, the severity of the disorder, the judgment of the attending physician and the like. In general, effective amounts for daily oral administration may be about 0.01 to 1,000 mg/kg, preferably about 0.5 to 500 mg/kg and effective amounts for parenteral administration may be about 0.1 to 100 mg/kg, preferably about 0.5 to 50 mg/kg.

In actual practice, the compounds of the invention are provided by administering the compound, or a precursor thereof, in a solid or liquid form; either neat or in combination with one or more conventional pharmaceutical carriers or excipients. Accordingly, the present invention provides a pharmaceutical composition which comprises a pharmaceutically acceptable carrier and an effective amount of a compound of formula I as described hereinabove.

The term "carrier", as used herein, shall encompass carriers, excipients, and diluents. Examples of carriers are well known to those skilled in the art and are prepared in accordance with acceptable pharmaceutical procedures, such as, for example, those described in Remington's Pharmaceutical Sciences, 17th edition, ed. Alfonoso R. Gennaro, Mack Publishing Company, Easton, Pa. (1985). Pharmaceutically acceptable carriers are those that are compatible with the other ingredients in the formulation and are biologically acceptable.

The compositions of the invention may be administered orally or parenterally, neat or in combination with conventional pharmaceutical carriers. Applicable solid carriers can include one or more substances which may also act as flavoring agents, lubricants, solubilizers, suspending agents, fillers, glidants, compression aids, binders or tablet-disintegrating agents or encapsulating materials. They are formulated in conventional manner, for example, in a manner similar to that used for known antihypertensive agents, diuretics and β-blocking agents. Oral formulations containing the active compounds of this invention may comprise any conventionally used oral forms, including tablets, capsules, buccal forms, troches, lozenges and oral liquids, suspensions or solutions. In powders, the carrier is a finely divided solid, which is an admixture with the finely divided active ingredient. In tablets, the active ingredient is mixed with a carrier having the necessary compression properties in suitable proportions and compacted in the shape and size desired. The powders and tablets preferably contain up to 99% of the active ingredient.

Capsules may contain mixtures of the active compound(s) with inert fillers and/or diluents such as the pharmaceutically acceptable starches (e.g. corn, potato or tapioca starch), sugars, artificial sweetening agents, powdered celluloses, such as crystalline and microcrystalline celluloses, flours, gelatins, gums, etc.

Useful tablet formulations may be made by conventional compression, wet granulation or dry granulation methods and utilize pharmaceutically acceptable diluents, binding agents, lubricants, disintegrants, surface modifying agents (including surfactants), suspending or stabilizing agents, including, but not limited to, magnesium stearate, stearic acid, sodium lauryl sulfate, talc, sugars, lactose, dextrin, starch, gelatin, cellulose, methyl cellulose, microcrystalline cellulose, sodium carboxymethyl cellulose, carboxymethylcellulose calcium, polyvinylpyrrolidine, alginic acid, acacia gum, xanthan gum, sodium citrate, complex silicates, calcium carbonate, glycine, sucrose, sorbitol, dicalcium phosphate, calcium sulfate, lactose, kaolin, mannitol, sodium chloride, low melting waxes and ion exchange resins. Preferred surface modifying agents include nonionic and anionic surface modifying agents. Representative examples of surface modifying agents include, but are not limited to, poloxamer 188, benzalkonium chloride, calcium stearate, cetostearl alcohol, cetomacrogol emulsifying wax, sorbitan esters, colliodol silicon dioxide, phosphates, sodium dodecylsulfate, magnesium aluminum silicate, and triethanolamine. Oral formulations herein may utilize standard delay or time release formulations to alter the absorption of the active compound(s). The oral formulation may also consist of administering the active ingredient in water or fruit juice, containing appropriate solubilizers or emulsifiers as needed.

Liquid carriers may be used in preparing solutions, suspensions, emulsions, syrups and elixirs. The active ingredient of this invention can be dissolved or suspended in a pharmaceutically acceptable liquid carrier such as water, an organic solvent, a mixture of both or pharmaceutically acceptable oils or fat. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (particularly containing additives as above, e.g., cellulose derivatives, preferably sodium carboxymethyl cellulose solution), alcohols (including monohydric alcohols and polyhydric alcohols, e.g., glycols) and their derivatives, and oils (e.g., fractionated coconut oil and arachis oil). For parenteral administration the carrier can also be an oily ester such as ethyl oleate and isopropyl myristate. Sterile liquid carriers are used in sterile liquid form compositions for parenteral administration. The liquid carrier for pressurized compositions can be halogenated hydrocarbon or other pharmaceutically acceptable propellant.

Liquid pharmaceutical compositions, which are sterile solutions or suspensions, can be utilized by, for example, intramuscular, intraperitoneal or subcutaneous injection. Sterile solutions can also be administered intravenously. Compositions for oral administration may be in either liquid or solid form.

Preferably the pharmaceutical composition is in unit dosage form, e.g., as tablets, capsules, powders, solutions, suspensions, emulsions, granules, or suppositories. In such form, the composition is sub-divided in unit dose containing appropriate quantities of the active ingredient; the unit dosage forms can be packaged compositions, for example, packeted powders, vials, ampoules, prefilled syringes or sachets containing liquids. The unit dosage form can be, for example, a capsule or tablet itself, or it can be the appropriate number of any such compositions in package form. Such unit dosage form may contain from about 1 mg/kg to about 250 mg/kg, and may given in a single dose or in two or more divided doses. Such doses may be administered in any manner useful in directing the active compounds herein to the recipient's bloodstream, including orally, via implants, parenterally (including intravenous, intraperitoneal and subcutaneous injections), rectally, vaginally, and transdermally. Such administrations may be carried out using the present compounds, or pharmaceutically acceptable salts thereof, in lotions, creams, foams, patches, suspensions, solutions, and suppositories (rectal and vaginal).

When administered for the treatment or inhibition of a particular disease state or disorder, it is understood that the effective dosage may vary depending upon the particular compound utilized, the mode of administration, the condition, and severity thereof, of the condition being treated, as well as the various physical factors related to the individual being treated. In therapeutic application, compounds of the present invention are provided to a patient already suffering from a disease in an amount sufficient to cure or at least partially ameliorate the symptoms of the disease and its complications. An amount adequate to accomplish this is defined as a "therapeutically effective amount". The dosage to be used in the treatment of a specific case must be subjectively determined by the attending physician. The variables involved include the specific condition and the size, age and response pattern of the patient.

In some cases it may be desirable to administer the compounds directly to the airways in the form of an aerosol. For administration by intranasal or intrabrochial inhalation, the compounds of this invention may be formulated into an aqueous or partially aqueous solution.

The compounds of this invention may be administered parenterally or intraperitoneally. Solutions or suspensions of these active compounds as a free base or pharmaceutically acceptable salt may be prepared in water suitably mixed with a surfactant such as hydroxyl-propylcellulose. Dispersions may also be prepared in glycerol, liquid polyethylene glycols and mixtures thereof in oils. Under ordinary conditions of storage and use, these preparations contain a preservative to inhibit the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

The compounds of this invention can be administered transdermally through the use of a transdermal patch. For the purposes of this disclosure, thransdermal administrations are understood to include all administrations across the surface of the body and the inner linings of bodily passages including epithelial and mucosal tissues. Such administrations may be carried out using the present compounds, or pharmaceutically acceptable salts thereof, in lotions, creams, foams, patches, suspensions, solutions, and suppositories (rectal and vaginal).

Transdermal administration may be accomplished through the use of a transdermal patch containing the active compound and a carrier that is inert to the active compound, is non-toxic to the skin, and allows delivery of the agent for systemic absorption into the blood stream via the skin. The carrier may take any number of forms such as creams and ointments, pastes, gels and occlusive devices. The creams and ointments may be viscous liquid or semisolid emulsions of either the oil-in-water or water-in-oil type. Pastes comprised of absorptive powders dispersed in petroleum or hydrophilic petroleum containing the active ingredient may also be suitable. A variety of occlusive devices may be used to release the active ingredient into the blood stream, such as a semi-permeable membrane covering a reservoir containing the active ingredient with or without a carrier, or a matrix containing the active ingredient. Other occlusive devices are known in the literature.

The compounds of this invention may be administered rectally or vaginally in the form of a conventional suppository. Suppository formulations may be made from traditional materials, including cocoa butter, with or without the addition of waxes to alter the suppository's melting point, and glycerin. Water soluble suppository bases, such as polyethylene glycols of various molecular weights, may also be used.

In certain embodiments, the present invention is directed to prodrugs. Various forms of prodrugs are known in the art, for example, as discussed in, for example, Bundgaard, (ed.), Design of Prodrugs, Elsevier (1985); Widder, et al. (ed.), Methods in Enzymology, vol. 4, Academic Press (1985);

Krogsgaard-Larsen, et al. (ed.), "Design and Application of Prodrugs", Textbook of Drug Design and Development, Chapter 5,113-191 (1991), Bundgaard, et al., Journal of Drug Deliver reviews, 8:1-38 (1992), Bundgaard, J. of Pharmaceutical Sciences, 77:285 et seq. (1988); and Higuchi and Stella (eds.) Prodrugs as Novel Drug Delivery Systems, American Chemical Society (1975).

It is understood that the dosage, regimen and mode of administration of these compounds will vary according to the malady and the individual being treated and will be subject to the judgment of the medical practitioner involved. It is preferred that the administration of one or more of the compounds herein begin at a low dose and be increased until the desired effects are achieved.

For a more clear understanding of the invention, and in order to illustrate the invention more clearly, specific examples thereof are set forth hereinbelow. The following examples are merely illustrative and are not to be understood as limiting the scope and underlying principles of the invention in any way. Various modifications of the invention, in addition to those described herein, will be apparent to those skilled in the art from the foregoing description. Such modifications are also intended to fall within the scope of the appended claims.

Unless otherwise stated, all parts are parts by weight. The following abbreviations are used: EtOH is ethanol, MeOH is methanol, EtOAc is ethyl acetate, IPA is isopropanol, $Et_3N$ is triethylamine, DMSO is dimethylsulfoxide, HPLC is high performance liquid chromatography, NMR is proton nuclear magnetic resonance, and MS is mass spectroscopy with (+) referring to the positive mode which generally gives a M+1 (or M+H) absorption where M designates the molecular mass.

EXAMPLE 1

Preparation of 8-(4-tert-Butylphenyl)-8-phenyl-2,3,4, 8-tetrahydroimidazol[1,5-a]pyrimidin-6-amine Step a) Ethyl-mandelimidate hydrochloride Under a nitrogen atmosphere, into a cold (0° C.) solution of benzaldehyde cyanohydrin (100 g, 0.75 mol) and ethanol in ether was added dropwise a freshly prepared ether-HCl solution (0.5 mol, 150 mL) over 30 minutes. The reaction mixture was stirred at 0° C. for 6 hours and then kept at 40° C. for 18 hours. The resulting suspension was diluted with hexanes and filtered. The filtercake was dried to give ethyl-mandelimidate hydrochloride as a light yellow solid (110 g, 82% yield, mp 116° C.). MS m/e (M+H)$^+$ 180.1; $^1$H NMR (400 MHZ, DMSOd$_6$) δ 1.22 (t, 3H), 3.64 (bs, 2H), 4.41 (m, 2H), 5.51 (s, 1H), 7.41 (m, 5H).

Step b) 2-(4,5,6,Tetrahydropyrimidyl)phenyl methanol

Under a nitrogen atmosphere, into a cold (0° C.) suspension of ethyl-mandelimidate hydrochloride (52 g, 0.241 mol) in ethanol was added dropwise diaminopropane (18.1 g, 0.241 mol) over 10 minutes. The suspension was heated at reflux temperature for 18 h, cooled to room temperature and concentrated in vacuo. Crystallization of the resultant residue from ethanol and isopropanol gave 2-(4,5,6,tetrahydropyrimidyl)phenyl methanol hydrochloride. The hydrochloride salt was dissolved in water and filtered. The filtrate was basified, with cooling, with NaOH (2.5 N, 30 mL) and filtered. The filtercake was air-dried to give 2-(4,5,6,tetrahydropyrimidyl) phenyl methanol as a white solid (36.5 g, 80% yield, mp 180° C.). MS m/e (M+H)$^+$ 191; $^1$H NMR (400 MHZ, DMSOd$_6$) δ 1.57 (m, 2H), 3.16 (m, 4H), 4.78 (s, 1H), 6.20 (bs, 2H), 7.30, (m, 3H), 7.38 (m, 2H).

Step c) 2-(4,5,6, Tetrahydropyrimidyl)phenyl ketone

Into a stirred suspension of 2-(4, 5, 6 tetrahydropyrimidyl) phenyl methanol (28.2 g, 0.148 mol) in methylene chloride was added all at once manganese oxide (50 mol). The mixture was stirred at room temperature for 48 h and filtered through solka floc. The filtercake was washed with chloroform. The filtrates were combined and concentrated. The resultant residue was crystallized from chloroform, ether and hexanes to afford 2-(4,5,6,-tetrahydropyrimidyl) phenyl ketone as a light yellow solid (26.1 g, 85% yield, mp 80° C.). MS m/e (M+H)$^+$ 189; $^1$H NMR (400 MHZ, DMSOd$_6$) δ 1.68 (m, 2H), 3.31 (m, 4H), 7.09 (s, 1H), 7.46 (m, 2H), 7.60, (m, 1H), 8.04 (m, 2H).

Step d) (4-tert-Butylphenyl)(phenyl)-1,4,5,6,-tetrahydropyrimidin-2-ylmethanol

Under a nitrogen atmosphere, CuI (50 mg) was added at room temperature to a freshly prepared 4-tert-butyl phenyl magnesium bromide [made by refluxing Mg (0.96 g, 39.31 mmol) and 1-bromo-tert-butylbenzene (8.49 g, 39.83 mmol) in THF (40 mL) for 4 hours] followed by a solution of 2-(4, 5,6,tetrahydropyrimidyl) phenyl ketone (example 1, step c, 3 g, 15.9 mmol) in THF (20 mL). The reaction mixture was heated at reflux temperature for 20 h, cooled to room temperature and concentrated in vacuo. The resultant residue was dispersed in aqueous $NH_4Cl$, acidified with HCl (6N, 16 mL) and extracted with ether. Under cooling, the aqueous phase was basified with $NH_4OH$ (30%, 50 mL) and extracted with chloroform. The chloroform extracts were combined, dried over $MgSO_4$ and concentrated in vacuo. Crystallization of this residue from isopropanol, gave (4-tert-butylphenyl)(phenyl)-1,4,5,6,-tetrahydropyrimidin-2-ylmethanol as a white solid (1.55 g, 30% yield, mp 151° C.). MS m/e (M+H)$^+$ 323.1; $^1$H NMR (400 MHZ, DMSOd$_6$) δ 1.27 (s, 9H), 1.64 (m, 2H) 3.24 (m, 4H), 6.4 (bs, 2H), 7.23-7.34 (m, 9H).

Step e) 2-[(4-tert-Butylphenyl)(chloro)phenylmethyl]-1,4, 5,6,-tetrahydropyrimidine Under a nitrogen atmosphere, into a cold (0° C.) solution of (4-tert-butylphenyl)(phenyl)-1,4,5,6,-tetrahydropyrimidin-2-ylmethanol (2.7 g, 8.37 mmol) in $CHCl_3$ was added $SOCl_2$ (1.9 mL) over 10 minutes. The reaction mixture was heated at reflux temperature for 4 h and concentrated in vacuo. The resultant residue was dissolved in benzene and concentrated in vacuo to dryness twice. The final residue was crystallized from chloroform and ether to afford 2-[(4-tert-butyl-phenyl) (chloro)phenylmethyl]-1,4,5,6,-tetrahydropyrimidine as an off white solid (2.4 g, 84% yield, mp 79° C.). MS m/e (M+H)$^+$ 341; $^1$H NMR (400 MHZ, DMSOd$_6$) δ 1.26 (s, 9H), 1.90 (m, 2H) 3.43 (m, 4H), 7.26 (d, 2H), 7.35 (m, 2H), 7.48 (m, 5H), 9.42 (bs, 1H).

Step f) (4-tert-Butylphenyl)(phenyl)-1,4,5,6,-tetrahydropyrimidin-2-ylmethylamine A solution of 2-[(4-tert-butylphenyl)(chloro)phenylmethyl]-1,4,5,6,-tetrahydropyrimidin (1 g, 2.65 mmol) in EtOH and a freshly prepared EtOH—$NH_3$ saturated solution (10 mL) was heated in a sealed vessel, at 60° C. for 24 h. The volatiles were removed in vacuo and the residue was dissolved in NaOH (2.5 N) and extracted with chloroform. The combined chloroform extracts were dried over $K_2CO_3$ and concentrated in vacuo to give (4-tert-butylphenyl)(phenyl)-1, 4,5,6,-tetrahydropyrimidin-2-ylmethylamine as a brown thick oil (0.76 g, 89%). MS m/e (M+H)$^+$ 322.2; $^1$H NMR (400 MHZ, DMSOd$_6$) δ 1.23 (s, 9H), 1.60 (m, 2H) 3.20 (m, 4H), 3.35 (bs, 3H), 7.18-7.38 (m, 9H).

Step g) 8-(4-tert-Butylphenyl)-8-phenyl-2,3,4,8-tetrahydroimidazol[1,5-a]pyrimidin-6-amine Under a nitrogen atmosphere, a solution of (4-tert-butylphenyl)(phenyl)-1,4,5,6,-tetrahydropyrimidin-2-ylmethylamine (0.76 g, 2.36 mmol) and cyanogen bromide (1.1 g, 9.45 mmol) in CHCl₃ was heated at reflux temperature for 40 h, cooled to room temperature and concentrated in vacuo. The resultant residue was dispersed in aqueous NH₄Cl, basified with NaOH (2.5 N) and extracted with chloroform. The organic extracts were combined, dried over K₂CO₃ and concentrated in vacuo. Purification of this residue by flash chromatography on silica gel (CH₂Cl₂/EtOAc/MeOH/Et₃N, 2/2/5.9/0.1) gave the title compound as a white solid (0.075 g, 9.1% yield); mp 139° C.); MS m/e (M−H)⁻ 345; ¹H NMR (400 MHZ, DMSOd₆) δ 1.22 (s, 9H), 1.66 (m, 2H,) 3.37 (m, 2H), 3.50 (m, 2H), 6.15 (bs, 2H), 7.20 (m, 1H), 7.22 (m, 4H), 7.40 (d, 2H), 7.52 (d, 2H).

EXAMPLE 2

Preparation of 8-(3-Benzylphenyl)-8-phenyl-2,3,4,8-tetrahydroimidazol[1,5-a]pyrimidin-6-amine Step a) 1-Benzyl-3-bromobenzene Under a nitrogen atmosphere, into a cold (10° C.) solution of trifluoroacetic acid (240 mL) was added a solution of 3-bromobenzophenone (11 g, 42.1 mmol) in CH₂Cl₂ (120 mL) over 10 minutes, followed by slow addition of NaBH₄-pellets (19 g) over 1 hour. The reaction mixture was stirred at room temperature for 18 h, poured into ice, basified with NaOH (50%) to pH 8 and extracted with ether. The organic extracts were combined, dried over MgSO₄, treated with charcoal and filtered. The filtrate was concentrated in vacuo to give 1-benzyl-3-bromobenzene as an oil (9.65 g, 92% yield) MS m/e (M+H)⁺ 248; ¹H NMR (400 MHZ, DMSOd₆) δ 3.89 (s, 2H,), 7.19-7.39 (m, 9H).

Step b) (3-Benzylphenyl)phenyl)-1,4,5,6-tetrahydropyrimidin-2-ylmethanol

Using essentially the same procedure described in Example, 1 step d, and employing 3-benzylphenyl)(bromo) magnesium and 2-(4,5,6,tetrahydropyrimidyl) phenyl ketone, a residue is obtained. Purification of this residue by flash chromatography on silica gel (CHCl₃/MeOH//Et₃N 1.9/8/0.1), and crystallization from isopropanol gave (3-benzylphenyl)phenyl)-1,4,5,6-tetrahydropyrimidin-2-ylmethanol as a white solid (1.2 g, 19% yield); m.p. 86° C.); MS m/e (M+H)⁺ 357.2; ¹H NMR (400 MHZ, DMSOd₆) δ 1.60 (m, 2H), 3.30 (m, 4H), 3.90 (s, 2H), 6.71 (bs, 2H), 7.19-7.29 (m, 14H).

Step c) 2-[(3-Benzyllphenyl)(chloro)phenylmethyl]-1,4,5,6,-tetrahydropyrimidine

Using essentially the same procedure described in Example, 1 step e, and employing (3-benzylphenyl)(phenyl) 1,4,5,6-tetrahydropyrimidin-2-ylmethanol, 2-[(3-benzyllphenyl)(chloro)phenylmethyl]-1,4,5,6,-tetrahydropyrimidine was obtained as a light brown solid (1.3 g, 91% yield, m.p. 70° C.). MS m/e (M+H)⁺ 375.1; ¹H NMR (400 MHZ, DMSOd₆) δ 1.90 (m, 2H), 3.43 (m, 4H), 3.99 (s, 2H), 7.21-7.48 (m, 14H), 9.44 (s, 2H).

Step d) (3-Benzylphenyl)(phenyl)-1,4,5,6,-tetrahydropyrimidin-2-ylmethylamine

Using essentially the same procedure described in Example, 1 step f, and employing 2-[(3-benzyllphenyl)(chloro)phenylmethyl]-1,4,5,6,-tetrahydropyrimidine, (3-benzylphenyl)(phenyl)-1,4,5,6,-tetrahydropyrimidin-2-ylmethylamine was obtained as a brown thick oil (0.85 g, 89% yield).); MS m/e (M+H)⁺ 356.1; ¹H NMR (400 MHZ, DMSOd₆) δ 1.55 (m, 2H), 3.16 (m, 4H), 3.88 (s, 2H), 6.15 (bs, 3H), 7.18-7.26 (m, 14H).

Step e) 8-(3-benzylphenyl)-8-phenyl-2,3,4,8-tetrahydroimidazol[1,5-a]pyrimidin-6-amine Using essentially the same procedure described in Example, 1 step g, and employing [(3-benzylphenyl)(phenyl)-1, 4, 5, 6,-tetrahydropyrimidin-2-ylmethylamine, and purifying by flash chromatography on silica gel (CH₂Cl₂/EtOAc/MeOH/Et₃N, 2/2/5.9/0.1), the title compound is obtained as a white solid (0.07 g, 8% yield, mp 80° C.); MS m/e (M−H)⁻ 379; ¹H NMR (400 MHZ, DMSOd₆) δ 1.65 (m, 2H), 3.37 (m, 2H), 3.51 (m, 2H), 6.50 (bs, 2H), 7.00 (m, 1H), 7.15 (m, 5H), 7.22 (m, 4H), 7.31 (m, 1H), 7.40 (m, 1H), 7.44 (m, 2H).

EXAMPLE 3

Preparation of 8-[3-(4-Fluorophenoxy)phenyl]-8-phenyl-2,3,4,8-tetrahydroimidazo[1,5-a]pyrimidin-6-amine Step a) [3-(4-Methoxybenzyl)phenyl](phenyl)1,4,5,6-tetrahydropyrimidin-2-ylmethanol Using essentially the same procedure described in Example, 1 step d, and employing bromo[3-(4-fluorophenoxy)phenyl]magnesium and purifying by flash chromatography on silica gel (CHCl₃/MeOH/Et₃N 1.9/8/0.1) and then by crystallization from isopropanol, [3-(4-methoxybenzyl)phenyl](phenyl)1,4,5,6-tetrahydropyrimidin-2-ylmethanol is obtained as a white solid (3.56 g, 71% yield, m.p. 64° C.).); MS m/e (M−H)⁻ 375.2; ¹H NMR (400 MHZ, DMSOd₆) δ 1.61 (m, 2H), 3.23 (bs, 4H), 6.89 (dd, 1H), 6.98 (m, 1H), 7.04 (m, 3H), 7.19 (d, 2H), 7.21 (m, 2H), 7.32 (m, 6H).

Step b) 2-{Chloro[3-(4-fluorophenoxy)phenyl]phenylmethyl}-1,4,5,6-tetrahydropyrimidine Using essentially the same procedure described in Example, 1 step e, and employing [3-(4-methoxybenzyl)phenyl](phenyl)1,4,5,6-tetrahydropyrimidin-2-ylmethanol, 2-{chloro[3-(4-fluorophenoxy)phenyl]phenylmethyl}-1,4,5,6-tetrahydropyrimidine is obtained as a light brown solid (1.4 g, 79% yield, m.p. 109° C.).); MS m/e (M+H)⁺ 395.1; ¹H NMR (400 MHZ, DMSOd₆) δ 1.90 (m, 2H), 3.44 (bs, 4H), 6.90 (t, 1H), 7.09 (m, 4H), 7.24 (m, 2H), 7.43 (m, 2H), 7.49 (m, 3H), 9.50 (s, 2H).

Step c) [3-(4-Fuorophenoxy)phenyl](phenyl)1,4,5,6-tetrahydropyrimidin-2-ylmethylamine Using essentially the same procedure described in Example, 1 step f, and employing 2-{chloro[3-(4-fluorophenoxy)phenyl]phenylmethyl}-1,4,5,6-tetrahydropyrimidine, afforded [3-(4-fuorophenoxy)phenyl](phenyl)1,4,5,6-tetrahydropyrimidin-2-ylmethylamine as an off white solid (0.635 g, 53% yield, mp 78° C.). MS m/e (M+H)⁺ 376; ¹H NMR (400 MHZ, DMSOd₆) δ 1.53 (m, 2H), 2.62 (bs, 2H), 3.17 (bs, 4H), 6.0 (bs, 1H), 6.82 (m, 1H), 7.01 (m, 4H), 7.19 (m, 3H), 7.21 (m, 3H), 7.29 (m, 2H).

Step d) 8-[3-(4-Fluorophenoxy)phenyl]-8-phenyl-2,3,4,8-tetrahydroimidazo[1,5-a]pyrimidin-6-amine Using essentially the same procedure described in Example, 1 step g and employing 3-(4-fluorophenoxy)phenyl](phenyl)1,4,5,6-tetrahydropyrimidin-2-ylmethylamine and purifying by flash chromatography on silica gel (CH₂Cl₂/EtOAc/MeOH/Et₃N, 2/2/5.9/0.1), the title product is obtained as a white solid (0.09 g, 13% yield, mp 165° C.); MS m/e (M+H)⁺ 401; ¹H NMR (400 MHZ, DMSOd₆) δ 1.74 (m, 2H), 3.40 (m, 2H), 3.63 (m, 2H,) 6.85 (dd, 1H), 7.02 (m, 2H), 7.14 (m, 1H), 7.18-7.32 (m, 7H), 7.40 (d, 2H), NH₂ is very broad resonance.

EXAMPLE 4

Preparation of 8-[3-(4-Methoxybenzyl)phenyl]-8-phenyl-2,3,4,8-tetrahydroimidazo[1,5-a]pyrimidin-6-amine Step a) 1-Bromo-3-(4-methoxybenzyl)benzene Using essentially the same procedure described in Example 2 step a and employing (3-bromophenyl)(4'-methoxyphenyl)methanone and purifying by flash chromatography on silica gel (hexane/EtOAC 95/5), 1-bromo-3-(4-methoxybenzyl)benzene is obtained as a colorless oil (15.2 g, 80% yield). MS m/e (M)$^+$ 276; $^1$H NMR (400 MHZ, DMSOd$_6$) δ 3.66 (s, 3H,), 3.82 (s, 2H), 6.82 (m, 2H), 7.17 (d, 2H), 7.19 (d, 2H), 7.35 (m, 2H).

Step b) [3-(4-Methoxybenzyl)phenyl](phenyl)1,4,5,6-tetrahydropyrimidin-2-ylmethanol Using essentially the same procedure described in Example, 1 step d, and employing 1-bromo[3-(4-methoxybenzyl)phenyl]magnesium and purifying by flash chromatography on silica gel (CHCl$_3$/MeOH/Et$_3$N 1.9/8/0.1) and then by crystallization from isopropanol, afforded) [3-(4-methoxybenzyl)phenyl]-(phenyl)1,4,5,6-tetrahydropyrimidin-2-ylmethanol as a white solid (2.2 g, 50% yield, m.p. 92° C.). MS m/e (M+H)$^+$ 387.1; $^1$H NMR (400 MHZ, DMSOd$_6$) δ 1.59 (m, 2H), 3.22 (bs, 4H), 6.20 (bs, 1H), 6.84 (d, 2H), 7.1 (m, 4H), 7.23 (m, 4H), 7.29 (m, 4H).

Step c) 2-{Chloro[3-(4-methoxybenzyl)phenyl]phenylmethyl}-1,4,5,6-tetrahydropyrimidine Using essentially the same procedure described in Example 1, step e, and employing 3-(4-methoxybenzyl)phenyl](phenyl)1,4,5,6-tetrahydropyrimidin-2-ylmethanol afforded 2-{chloro[3-(4-methoxybenzyl)phenyl]phenylmethyl}-1,4,5,6-tetrahydropyrimidine as a light brown solid (1.65 g, 81% yield, m.p. 125° C.). MS m/e (M+H)$^+$ 405.1; $^1$H NMR (400 MHZ, DMSOd$_6$) δ 1.90 (m, 2H), 3.44 (bs, 4H), 3.71 (s, 3H), 3.92 (s, 2H), 6.85 (dd, 2H), 7.12 (d, 2H), 7.17 (m, 1H), 7.23 (m, 1H), 7.34 (m, 3H), 7.41 (t, 1H), 7.49 (m, 3H), 9.44 (s, 1H).

Step d) [3-(4-Methoxybenzyl)phenyl](phenyl)1,4,5,6-tetrahydropyrimidin-2-ylmethylamine Using essentially the same procedure described in Example, 1 step f and employing 2-{chloro[3-(4-methoxybenzyl)phenyl]phenylmethyl}-1,4,5,6-tetrahydropyrimidine, gave [3-(4-methoxybenzyl)phenyl](phenyl)1,4,5,6-tetrahydropyrimidin-2-ylmethylamine as a brown thick oil (1.55 g, 98% yield). MS m/e (M+H)$^+$ 386.7; $^1$H NMR (400 MHZ, DMSOd$_6$) δ 1.52 (m, 2H), 3.12 (m, 4H), 3.27 (bs, 3H), 3.66 (s, 3H), 3.77 (s, 2H), 6.79 (d, 2H), 7.06 (m, 1H), 7.08 (d, 2H), 7.22 (m, 8H).

Step e) 8-[3-(4-Methoxybenzyl)phenyl]-8-phenyl-2,3,4,8-tetrahydroimidazo[1,5-a]pyrimidin-6-amine Using essentially the same procedure described in Example, 1, step g, and employing [3-(4-methoxybenzyl)phenyl](phenyl)1,4,5,6-tetrahydropyrimidin-2-ylmethylamine and purifying by flash chromatography on silica gel (CH$_2$Cl$_2$/EtOAc/MeOH/Et$_3$N, 2/2/5.9/0.1), the title product is obtained as a white solid (0.13 g, 8% yield, mp 132° C.); MS m/e (M+H)$^+$ 411; $^1$H NMR (400 MHZ, DMSOd$_6$) δ 1.66 (m, 2H), 3.36 (m, 2H), 3.51 (m, 2H), 3.69 (s, 3H), 3.79 (s, 2H), 6.30 (bs, 2H), 6.81 (d, 2H), 6.97 (d, 1H), 7.14 (d, 2H), 7.16 (q, 2H), 7.22 (m, 2H), 7.30 (md, 1H), 7.38 (m, 1H), 7.44 (d, 2H).

EXAMPLE 5

Preparation of 8-[3-(4-Fluorobenzyl)phenyl]-8-phenyl-2,3,4,8-tetrahydroimidazo[1,5-a]pyrimidin-6-amine Step a) 1-Bromo-3-(4-fluorobenzyl)benzene Using essentially the same procedure described in Example 2, step a, and employing (3-bromophenyl)(4-fluorophenyl)methanone and purifying by flash chromatography on silica gel (hexane/EtOAC 95/5), 1-bromo-3-(4-fluorobenzyl)benzene is obtained as a colorless oil (15.2 g, 80% yield). MS m/e (M)$^+$ 266; $^1$H NMR (400 MHZ, DMSOd$_6$) δ 3.92 (s, 2H,), 7.08 (m, 2H), 7.23 (m, 4H), 7.36 (m, 1H), 7.43 (bs, 1H).

Step b) [3-(4-Fluorobenzyl)phenyl](phenyl)1,4,5,6-tetrahydropyrimidin-2-ylmethanol Using essentially the same procedure described in Example 1, step d, and employing 1-bromo[3-(4-fluorobenzyl)phenyl]magnesium and purifying by flash chromatography on silica gel (CH$_2$Cl$_2$/EtOAc/IPA/Et$_3$N 3.9/2/4/0.1) and then by crystallization from isopropanol, [3-(4-fluorobenzyl)phenyl](phenyl)1,4,5,6-tetrahydropyrimidin-2-ylmethanol is obtained as a white solid (2.2 g, 77% yield, mp 60° C.). MS m/e (M+H)$^+$ 375.2; $^1$H NMR (400 MHZ, DMSOd$_6$) δ 1.62 (m, 2H), 3.23 (bs, 4H), 3.90 (s, 2H), 6.80 (bs, 2H), 7.09 (m, 4H), 7.20 (m, 4H), 7.29 (m, 5H).

Step c) 2-{Chloro[3-(4-fluorobenzyl)phenyl]phenylmethyl}-1,4,5,6-tetrahydropyrimidine Using essentially the same procedure as described in Example 1, step e, and employing [3-(4-fluorobenzyl)phenyl](phenyl)1,4,5,6-tetrahydropyrimidin-2-ylmethanol, 2-{chloro[3-(4-fluorobenzyl)phenyl]phenylmethyl}-1,4,5,6-tetrahydropyrimidine is obtained as a light yellow solid (2.2 g, 98% yield, mp 74° C.). MS m/e (M+H)$^+$ 393.1; $^1$H NMR (400 MHZ, DMSOd$_6$) δ 1.89 (m, 2H), 3.40 (m, 4H), 3.94 (s, 2H), 7.05 (m, 2H), 7.19 (m, 4H), 7.21 (m, 3H), 7.38 (t, 1H), 7.45 (m, 3H), 9.40 (s, 1H).

Step d) [[3-(4-Fluorobenzyl)phenyl](phenyl)1,4,5,6-tetrahydropyrimidin-2-ylmethyl]amine Using essentially the same procedure as described in Example 1, step f, and employing 2-{chloro[3-(4-fluorobenzyl)phenyl]phenylmethyl}-1,4,5,6-tetrahydropyrimidine, a residue was obtained. Purification of the residue by flash chromatography on silica gel (CH$_2$Cl$_2$/EtOAc/IPA/Et$_3$N 1.9/2/6/0.1) gave [[3-(4-fluorobenzyl)phenyl]-(phenyl)1,4,5,6-tetrahydropyrimidin-2-ylmethyl]amine as a thick yellow oil (1.35 g, 64% yield). MS m/e (M+H)$^+$ 374.2; $^1$H NMR (400 MHZ, DMSOd$_6$) δ 1.53 (m, 2H), 2.65 (bs, 2H), 3.17 (m, 4H), 3.87 (s, 2H), 6.0 (bs, 1H), 7.0-7.25 (m, 13H).

Step e) 8-[3-(4-Fluorobenzyl)phenyl]-8-phenyl-2,3,4,8-tetrahydroimidazo[1,5-a]pyrimidin-6-amine Using essentially the same procedure as described in Example 1, step g, and employing [[3-(4-fluorobenzyl)phenyl](phenyl)1,4,5,6-tetrahydropyrimidin-2-ylmethyl]amine, a residue was obtained. Purification of the residue by flash chromatography on silica gel (CH$_2$Cl$_2$/EtOAc/MeOH/Et$_3$N, 2/2/5.9/0.1) gave 8-[3-(4-fluorobenzyl)phenyl]-8-phenyl-2,3,4,8-tetrahydroimidazo[1,5-a]pyrimidin-6-amine as a white solid (0.30 g, 21% yield, mp 152° C.); MS m/e (M+H)$^+$ 399; $^1$H NMR (400 MHZ, DMSOd$_6$) δ 1.66 (m, 2H), 3.35 (m, 2H), 3.52 (m, 2H), 3.86 (s, 2H), 6.50 (bs, 2H), 6.99 (d, 1H), 7.07 (m, 2H), 7.17 (m, 4H), 7.22 (m, 2H), 7.23 (m, 1H), 7.36 (m, 1H), 7.43 (d, 2H).

EXAMPLE 6

Preparation of 8-Phenyl-8-[3-(trifluoromethyl)phenyl]-2,3,4,8-tetrahydroimidazo[1,5-a]pyrimidin-6-amine Step a) 3-Trifluromethylphenylmagnesium bromide Into a solution containing 3-bromo-trifluromethylbenzene (15 g, 65, mmol) and THF (50 mL) was added magnesium metal (1.6 g, 66 mmol). The reaction was heated to reflux 18 hours. Then cooled to room temperature and used immediately.

Step b) Phenyl-(1,4,5,6-tetrahydro-pyrimidin-2-yl)-3-trifluromethylphenyl)-methanol Into the above-prepared Gringnard solution was added CuI (0.8 g, 4.4 mmol) at room temperature followed by 2-(4,5,6-tetrahydropyrimidyl) phenyl ketone, (5 g, 26.5 mmol). The reaction was heated to reflux for 18 h and concentrated in vacuo. The resultant residue was taken in 1 N HCl, washed with ether, basified with solid $NaHCO_3$ and extracted with ethyl acetate. The organic extracts were combined, dried over $MgSO_4$ and concentrated to dryness to afford phenyl-(1,4,5,6-tetrahydro-pyrimidin-2-yl)-3-trifluromethyl-phenyl)-methanol as an off white solid (5 g, 57% yield). MS m/e 255 $(M)^+$; $^1HNMR$ (DMSO-$d_6$, 300 MHz) δ 1.75 (m, 2H), 3.3 (m, 4H), 7.4 (m, 5H), 7.65 (m, 4H).

Step c) 2-[(3-Trifluromethylphenyl)(chloro)phenylmethyl]-1,4,5,6,-tetrahydropyrimidine A solution of Phenyl-(1,4,5,6-tetrahydro-pyrimidin-2-yl)-3-trifluromethylphenyl)-methanol (4.5 g, 13 mmol) in $CHCl_3$ was treated with $SOCl_2$ (3 mL) heated at reflux temperature for 4 h, cooled to room temperature and concenterated in vacuo to give 2-[(3-trifluromethylphenyl)(chloro)phenylmethyl]-1,4,5,6,-tetrahydropyrimidine as a yellow solid (4.5 g, 96% yield). MS m/e 255 $(M)^+$; $^1HNMR$ (DMSO-$d_6$, 300 MHz) δ 1.95 (m, 2H), 3.5 (m, 5H), 7.39 (m, 2H), 7.5 (m, 3H), 7.7 (m, 2H), 7.85 (m, 1H), 9.6 (b, 2H).

Step d) 2-[(3-Trifluromethylphenyl)(phenyl)]-1,4,5,6,-tetrahydropyrimidin-2-ylmethylamine Into a container, cooled to −30° C., was added 2-[(3-trifluromethylphenyl)-(chloro)phenylmethyl]-1,4,5,6,-tetrahydropyrimidine (2 g, 5.6 mmol) and ammonia dissolved in isopropyl alcohol 8 N (20 mL). The container was sealed, heated to 60° C. for 16 h and cooled to room temperature. The reaction mixture was removed and concentrated in vacuo. The residue was dispersed in 2.5 N NaOH and extracted with $CH_2Cl_2$. The extracts were combined, dried over $MgSO_4$, and concentrated in vacuo to give 2-[(3-trifluromethylphenyl)(phenyl)]-1,4,5,6,-tetrahydropyrimidin-2-ylmethylamine as a brown oil (1.5 g. MS m/e 334 $(M)^+$.

Step e) 8-Phenyl-8-[3-(trifluoromethyl)phenyl]-2,3,4,8-tetrahydroimidazo[1,5-a]pyrimidin-6-amine A solution of 2-[(3-trifluromethylphenyl)(phenyl)]-1,4,5,6,-tetrahydropyrimidin-2-ylmethylamine (1.3 g, 3.9 mmol) in $CHCl_3$ was treated with BrCN (1.6 g, 15.6 mmol), heated at reflux temperature for 48 h, cooled to room temperature and poured into NaOH 2.5 N. The phases were separated and the aqueous phase was extracted with $CHCl_3$. The extracts were combined with the original organic phase, dried over $MgSO_4$ and concenterated to dryness. The resultant residue was purified by flash chromatography on silica gel in; isopropyl alcohol/ethanol/methylene chloride/triethyl amine (6:2:2:1 drop) to give the title product as a light brown solid (0.2 g, 20% yield) was recovered. MS m/e 357 $(M)^-$; $^1HNMR$ (DMSO-$d_6$, 300 MHz) δ 1.75 (m, 2H), 3.4 (m, 2H), 3.6 (m, 2H), 7.2 (m, 3H), 7.5 (m, 4H), 7.95 (m, 2H).

EXAMPLE 7

Preparation of 8-(3-Methoxyphenyl)-8-phenyl-2,3,4,8-tetrahydroimidazo[1,5-a]pyrimidin-6-amine Step a) Phenyl-(1,4,5,6-tetrahydro-pyrimidin-2-yl)-3-methoxy-phenyl)-methanol Using essentially the same procedure described in Example 6, step b, and employing 2-(4,5,6-tetrahydropyrimidyl) phenyl ketone and 3-methoxy-phenyl magnesium bromide, phenyl-(1,4,5,6-tetrahydro-pyrimidin-2-yl)-3-methoxy-phenyl)-methanol was obtained as a light brown solid. $^1HNMR$ (DMSO-$d_6$, 300 MHz) δ 1.8 (m, 2H), 3.4 (m, 4H), 3.75 (s, 3H), 6.95 (m, 3H), 7.3 (m, 3H), 7.4 (m, 3H).

Step b) 2-[(3-Methoxy-phenyl)(chloro)phenylmethyl]-1,4,5,6,-tetrahydropyrimidin

Using essentially the same procedure described in Example 6, step c, and employing phenyl-(1,4,5,6-tetrahydro-pyrimidin-2-yl)-3-methoxy-phenyl)-methanol, 2-[(3-methoxy-phenyl)(chloro)phenylmethyl]-1,4,5,6,-tetrahydropyrimidin was obtained as a brown solid. $^1HNMR$ (DMSO-$d_6$, 300 MHz) δ 1.95 (m, 2H), 3.4 (m, 4H), 3.75 (s, 3H), 6.8 (s, 1H), 6.9 (dd, 1H), 7.1 (dd, 1H), 7.4 (m, 4H), 7.5 (m, 4H), 9.4 (b, 2H).

Step c) 2-[(3-Methoxyphenyl)(phenyl)]-1,4,5,6,-tetrahydropyrimidin-2-ylmethylamine Using essentially the same procedure described in Example 6, step d, and employing 2-[(3-methoxyphenyl)(chloro)phenylmethyl]-1,4,5,6,-tetrahydropyrimidine, 2-[(3-methoxyphenyl)(phenyl)]-1,4,5,6,-tetrahydropyrimidin-2-ylmethylamine was obtained as a brown oil. MS m/e 296 $(M)^+$.

Step d) 8-(3-methoxyphenyl)-8-phenyl-2,3,4,8-tetrahydroimidazo[1,5-a]pyrimidin-6-amine Using essentially the same procedure described in Example 6, step e, and employing 2-[(3-methoxyphenyl)(phenyl)]-1,4,5,6,-tetrahydropyrimidin-2-ylmethylamine, the title compound was obtained as a white solid. MS m/e 319 $(M)^-$; $^1HNMR$ (DMSO-$d_6$, 300 MHz) δ 1.6 (m, 2H), 3.3 (m, 2H), 3.5 (m, 2H), 3.6 (s, 3H), 6.7 (m, 1H), 7.05 (m, 2H), 7.1 (m, 2H), 7.1 (m, 2H), 7.4 (d, 2H).

EXAMPLE 8

Preparation of 7-(4-Methoxy-3-methylphenyl)-7-(3-propoxyphenyl)-2,7-dihydro-3H-imidazo[1,5-a]imidazol-5-amine Step a) Ethyl 2-hydroxy-2-(4-methoxy-3-methylphenyl)ethanimidoate hydrochloride A mixture of 4-methoxy-3-methylbenzaldehyde (17.6 mL) and trimethylsilyl cyanide (18.7 mL) was treated with zinc iodide (0.600 g), stirred for 3 h, treated with diethyl ether and filtered through a cellite pad. The filtrate was evaporated. The resultant residue was dissolved in absolute ethanol, cooled to −20° C. and saturated with gaseous hydrogen chloride (40 g). The solution was slowly warmed up to room temperature and concentrated in vacuo. The resultant residue was triturated with diethyl ether and filtered. The filtercake was dried under vacuum to give ethyl 2-hydroxy-2-(4-methoxy-3-methylphenyl)ethanimidoate hydrochloride as a yellow solid (28.55 g), characterized by LCMS analysis. LCMS Conditions: HP 1100 HPLC system; Waters Xterra MS C18, 2 mm (i.d.)×50 mm (length), 3.5 um column, set at 50° C.; Flow rate 1.0 mL/min; Solvent A: 0.02% $NH_4OH$ in water; Solvent B 0.02% $NH_4OH$ in ACN; Gradient: Time O: 10% B; 2.5 min 90% B; 3 min 90% B; Sample concentration: ~2.0 mM; Injection volume: 5 uL; Detection: 220 nm, 254 nm DAD.

Step b) [4,5-Dihydro-1H-imidazol-2-yl(4-methoxy-3-methylphenyl)(3-propoxyphenyl)methyl]amine Using a procedure analogous to the one disclosed in U.S. Pat. No. 3,926,994 and employing ethyl 2-hydroxy-2-(4-methoxy-3-methylphenyl)ethanimidoate hydrochloride salt with 1,2-ethyldiamine, and subsequent reaction with 3-propyloxy phenylmagnesium bromide was dissolved in chloroform (20 mL) gave a reaction mixture. Diisopropylethylamine (2 mL) was added to the reaction mixture, followed by thionyl chloride (1 mL). After 1 hour the reaction mixture was diluted with acetonitrile and cooled to −78° C. The reaction solution was saturated with gaseous ammonia (20 g). The flask was sealed and warmed up to room temperature. After 1 hour the solution was again cooled down to −78° C. and the ammonia was slowly evaporated. Following the removal of ammonia, the remaining solvents were evaporated and the residue was taken up in ethyl acetate, filtered through a pad of silica. The silica pad was eluted with ethyl acetate, then with (40/5/5) ethyl acetate/methanol/ammonium hydroxide. The eluents were combined and concentrated in vacuo to afford [4,5-Dihydro-1H-imidazol-2-yl(4-methoxy-3-methylphenyl)(3-propoxyphenyl)methyl]amine as a yellow amorphous solid (0.6 g), characterized by LCMS analysis. LCMS Conditions: HP 1100 HPLC system; Waters Xterra MS C18, 2 mm (i.d.)×50 mm (length), 3.5 um column, set at 50° C.; Flow rate 1.0 mL/min; Solvent A: 0.02% NH$_4$OH in water; Solvent B 0.02% NH$_4$OH in ACN; Gradient: Time O: 10% B; 2.5 min 90% B; 3 min 90% B; Sample concentration: ~2.0 mM; Injection volume: 5 uL; Detection: 220 nm, 254 nm DAD.

Step c) 7-(4-Methoxy-3-methylphenyl)-7-(3-propoxyphenyl)-2,7-dihydro-3H-imidazo[1,5-a]imidazol-5-amine A solution of [4,5-dihydro-1H-imidazol-2-yl(4-methoxy-3-methylphenyl)(3-propoxyphenyl)methyl]amine (0.6 g) in chloroform is treated with cyanogen bromide (0.581 g), heated at 60° C. for 5 days and filtered through a pad of silica. The silica pad was eluted with ethyl acetate, followed by elution with (40:5:5) ethyl acetate: methanol: ammonium hydroxide. The eluents were combined and concentrated in vacuo to give a thick yellow oil, which was purified by Gilson preparative reverse phase HPLC system YMC Pro C18, 20 mm×50 mm ID, 5 uM column; 2 mL injection; Solvent A: 0.02% NH$_4$OH/water; Solvent B:0.02% NH$_4$OH/acetonitrile; Gradient: Time O: 95% A; 2 min: 95% A; 14 min: 10% A, 15 min: 10% A, 16 min: 95% A; Flow rate 22.5 mL/min; Detection: 254 nm DAD to afford the title compound was as an off-white, amphorous solid (0.131 g), characterized by LCMS analysis. LCMS Conditions: HP 1100 HPLC system; Waters Xterra MS C18, 2 mm (i.d.)×50 mm (length), 3.5 um column, set at 50° C.; Flow rate 1.0 mL/min; Solvent A: 0.02% NH$_4$OH in water; Solvent B 0.02% NH$_4$OH in ACN; Gradient: Time O: 10% B; 2.5 min 90% B; 3 min 90% B; Sample concentration: ~2.0 mM; Injection volume: 5 uL; Detection: 220 nm, 254 nm DAD; retention time: 2.34 min, [M−H] 377, [M+H] 379.

EXAMPLE 9

Preparation of 8-(4-Methoxy-3-methylphenyl)-8-(3-propoxyphenyl)-2,3,4,8-tetrahydroimidazo[1,5-a] pyrimidin-6-amine Using essentially the same procedure described in Example 8 and employing 1,3-propyldiamine in place of 1,2-ethyldiamine, the title compound was obtained as an off-white, amorphous solid, characterized by LCMS analysis. LCMS Conditions: HP 1100 HPLC system; Waters Xterra MS C18, 2 mm (i.d.)×50 mm (length), 3.5 um column, set at 50° C.; Flow rate 1.0 mL/min; Solvent A: 0.02% NH$_4$OH in water; Solvent B 0.02% NH$_4$OH in ACN; Gradient: Time O: 10% B; 2.5 min 90% B; 3 min 90% B; Sample concentration: ~2.0 mM; Injection volume: 5 uL; Detection: 220 nm, 254 nm DAD; (retention time: 2.43 min, [M−H] 391, [M+H] 393.

EXAMPLE 10

Preparation of 8-(4-Methoxy-3-methylphenyl)-3,3-dimethyl-8-(3-propoxyphenyl)-2,3,4,8-tetrahydroimidazo[1,5-a]pyrimidin-6-amine Using essentially the same procedure described in Example 8 and employing 1,3-diamino-2,2-dimethylpropane in place of 1,2-ethyldiamine, the title compound was obtained as an off-white, amorphous solid, characterized by LCMS analysis. LCMS Conditions: HP 1100 HPLC system; Waters Xterra MS C18, 2 mm (i.d.)×50 mm (length), 3.5 um column, set at 50° C.; Flow rate 1.0 mL/min; Solvent A: 0.02% NH$_4$OH in water; Solvent B 0.02% NH$_4$OH in ACN; Gradient: Time O: 10% B; 2.5 min 90% B; 3 min 90% B; Sample concentration: ~2.0 mM; Injection volume: 5 uL; Detection: 220 nm, 254 nm DAD; (retention time: 2.74 min, [M−H] 419, [M+H] 421).

EXAMPLE 11

Preparation of 8,8-Diphenyl-2,3,4,8-tetrahydroimidazo[1,5a]pyrimidin-6-amine

Using essentially the same procedure described in Example 8 and employing benzaldehyde, 1,3-propyldiamine and phenylmagnesium bromide, the title compound is obtained, $^1$H NMR (400 MHZ, DMSOd$_6$) δ 1.62 (m, 2H), 3.4 (t, 2H), 3.58 (t, 2H), 6.2 (brs, 2H), 7.15 (m, 2H), 7.3 (m, 4H), 7.55 (m, 4H); MS m/e (M)$^+$ 291.

EXAMPLE 12

Preparation of 8-[3-(2-Cyclopropyl-ethyl)-phenyl]-8-(4-trifluoromethoxy-phenyl)-2,3,4,8-tetrahydro-imidazo[1,5-a]pyrimidin-6-ylamine

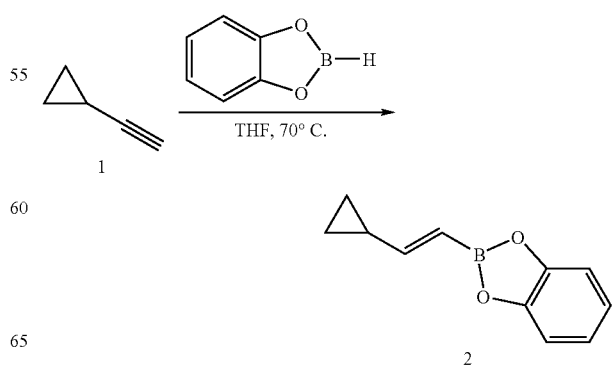

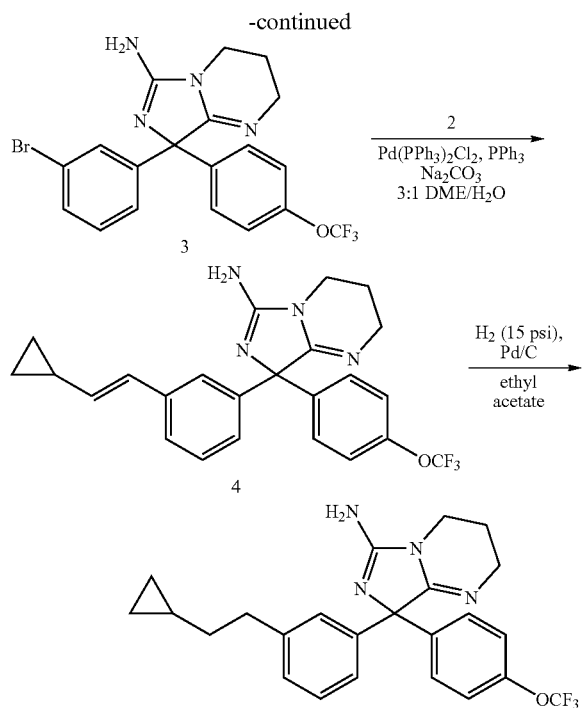

Preparation of Compound 2

A mixture of 3-cyclopropyl-1-propyne (1.00 g, 15.1 mmol) and catechol borane (2.72 g, 22.6 mmol) in tetrahydrofuran (70 mL) was heated at reflux for 3 h, cooled to room temperature and concentrated. Purification by flash chromatography (silica 1:1 hexanes/ethyl acetate afforded 1.05 g of 2 as a colorless syrup which was ~50% pure as determined by $^1$H NMR: $^1$H NMR (300 MHz, CDCl$_3$) δ 7.22-7.16 (m, 2H), 7.08-7.02 (m, 2H), 6.45 (dd, J=17.8, 9.4 Hz, 1H), 5.84 (d, J=17.8 Hz, 1H), 1.72-1.62 (m, 1H), 0.98-0.89 (m, 2H), 0.68-0.61 (m, 2H).

Preparation of Compound 4

A mixture of 3 (0.106 g, 0.23 mmol), 2 (0.130 g, ~50% purity, 0.35 mmol), bis(triphenylphosphino)palladium(II) chloride (0.008 g, 0.011 mmol), triphenylphosphine (0.006 g, 0.023 mmol) and sodium carbonate (0.073 g, 0.69 mmol) in 3:1 DME/water (8 mL) was heated at 80° C. for 2 h. The reaction was cooled to room temperature, concentrated and the residue diluted with ethyl acetate (50 mL) and water (20 mL). The organic layer was separated and washed with brine (20 mL), dried over sodium sulfate, filtered and concentrated. Purification by flash chromatography (silica, 95:5:0.5 methylene chloride/methanol/concentrated ammonium hydroxide) afforded 4 (0.073 g 72%) as a white solid: $^1$H NMR (300 MHz, CDCl$_3$) δ 7.47 (d, J=8.8 Hz, 2H), 7.36 (br s, 1H), 7.27-7.18 (m, 3H), 7.12 (d, J=8.6 Hz, 2H), 6.42 (d, J=15.7 Hz, 1H), 5.69 (dd, J 15.7, 8.9 Hz, 1H), 3.68-3.53 (m, 4H), 2.00-1.85 (m, 2H), 1.58-1.48 (m, 1H), 0.82-0.77 (m, 2H), 0.50-0.44 (m, 2H); ESI MS m/z 441 [C$_{24}$H$_{23}$F$_3$N$_4$O+H]$^+$.

Preparation of 8-[3-(2-Cyclopropyl-ethyl)-phenyl]-8-(4-trifluoromethoxy-phenyl)-2,3,4,8-tetrahydro-imidazo[1,5-a]pyrimidin-6-ylamine A mixture of 4 (0.073 g, 0.16 mmol) and palladium on carbon (0.020 g, 10 wt %, wet) in ethyl acetate was shaken under an atmosphere of hydrogen (15 psi) for 2.75 h. The reaction mixture was filtered through celite and the filtrate concentrated. Purification by flash chromatography (silica, 95:5:0.5 methylene chloride/methanol/concentrated ammonium hydroxide) followed by freeze-drying from acetonitrile/water (1:1, 4 mL) afforded 0.038 g of a white solid. This solid was further purified by semi-preparative chromatography (method 3), the appropriate fractions were combined and neutralized with 10% aqueous sodium carbonate. The acetonitrile was removed under reduced pressure and the residue extracted with methylene chloride (3×20 mL). The combined organic layers were washed with brine (25 mL), dried over sodium carbonate, filtered and concentrated and then freeze-dried from acetonitrile/water (1:1, 4 mL) to afford the title product as a white solid, 0.024 g (33% yield), mp 65-77° C.; $^1$H NMR (500 MHz, CD$_3$OD) δ 7.42 (d, J=8.8 Hz, 2H), 7.23-7.10 (m, 6H), 3.69 (t, J=6.0 Hz, 2H), 3.47 (t, J=5.5 Hz, 2H), 2.66 (t, J=7.5 Hz, 2H), 1.90-1.82 (m, 2H), 1.45 (dd, J=15.0, 7.0 Hz, 2H), 0.68-0.61 (m, 1H), 0.38-0.34 (m, 2H), −0.01--0.03 (m, 2H); ESI MS m/z 443 [C$_{24}$H$_{25}$F$_3$N$_4$O+H]$^+$.

EXAMPLE 13

Preparation of 8-(3-Allylphenyl)-8-(4-trifluoromethoxyphenyl)-2,3,4,8-tetrahydro-imidazo[1,5-a]pyrimidin-6-ylamine

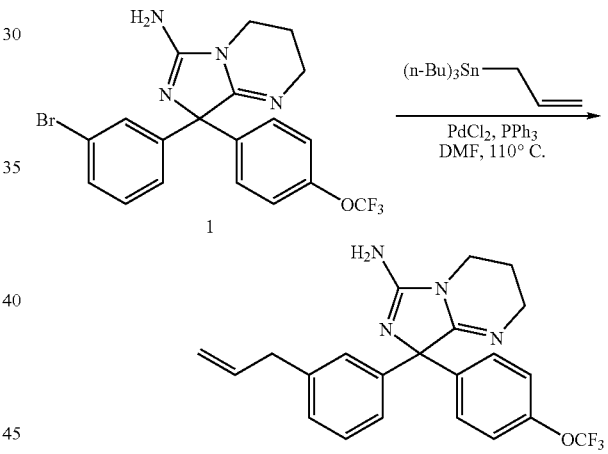

A mixture of 1 (0.700 g, 1.54 mmol), allyltributyltin (0.611 g, 1.85 mmol), palladium chloride (0.013 g, 0.08 mmol) and triphenylphosphine (0.081 g, 0.31 mmol), in DMF (6.0 mL) was degassed then heated at 110° C. for 17 h. The mixture was cooled to room temperature, diluted with diethyl ether (100 mL) and washed with water (2×30 mL) and brine (50 mL), dried over sodium sulfate, filtered and concentrated. Purification by flash chromatography (silica, 97:2.5:0.5 methylene chloride/methanol/concentrated ammonium hydroxide) afforded 2 (0.353 g, 55%) as a white solid. A portion (0.065 g) of this material was further purified by semi-preparative LC (Method 3). The appropriate fractions were combined and neutralized with saturated aqueous sodium carbonate (10 mL), most of the acetonirile was removed and the mixture then extracted with methylene chloride (3×25 mL). The combined organic layers were dried over sodium sulfate, filtered and concentrated and then freeze-dried from 2:1 acetonitrile/water (3 mL) to afford the title product as a white solid, 0.027 g, mp 89-111° C.; $^1$H NMR (500 MHz, CD$_3$OD) δ 7.42 (d, J=6.9 Hz, 2H), 7.25-7.10 (m, 6H), 5.96-5.88 (m, 1H), 5.07-

4.99 (m, 2H), 3.68 (t, J=5.9 Hz, 2H), 3.47 (t, J=4.6 Hz, 2H), 3.34-3.29 (m, 2H), 1.88-1.84 (m, 2H); ESI MS m/z 415 [$C_{22}H_{21}F_3N_4O$+H]$^+$.

EXAMPLE 14

Preparation of 8-(3-Propyl-phenyl)-8-(4-trifluoromethoxy-phenyl)-2,3,4,8-tetrahydro-imidazo[1,5-a]pyrimidin-6-ylamine

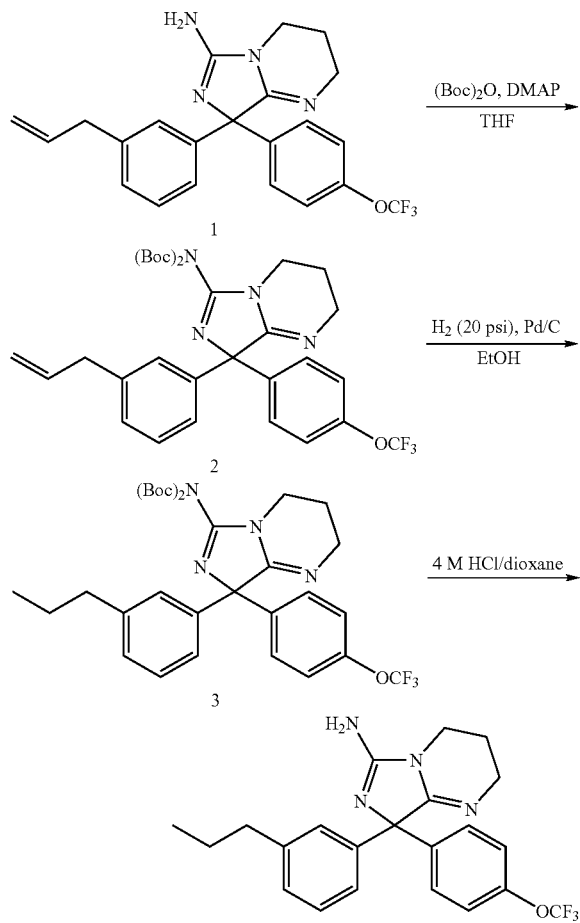

Preparation of Compound 2

A mixture of 1 (0.288 g, 0.70 mmol), 4-dimethylaminopyridine (0.085 g, 0.70 mmol) and di-tert-butyldicarbonate (0.379 g, 1.74 mmol) in tetrahydrofuran (10 mL) was stirred at room temperature for 17 h. The mixture was diluted with methylene chloride (75 mL) and washed with 1 N citric acid solution (2×25 mL) and brine (50 mL), dried over sodium sulfate, filtered and concentrated to afford 2 (0.38 g, 89%) as a yellow oil: $^1$H NMR (500 MHz, CDCl$_3$) δ 7.57 (d, J=8.7 Hz, 2H), 7.43-7.15 (m, 6H), 5.96-5.88 (m, 1H), 5.07-5.02 (m, 2H), 3.76-3.67 (m, 4H), 3.37 (d, J=6.7 Hz, 2H), 1.89-1.83 (m, 2H), 1.37 (s, 18H); ESI MS m/z 615 [$C_{32}H_{37}F_3N_4O_5$+H]$^+$.

Preparation of Compound 3

A mixture of 2 (0.088 g, 0.14 mmol) and palladium on carbon (0.020 g, 10 wt %, wet) in ethanol was shaken under an atmosphere of hydrogen (20 psi) for 1 h. The reaction mixture was then filtered through celite and the filtrate concentrated to afford 3 (0.075 g, 86%) as a colorless oil: $^1$H NMR (500 MHz, CDCl$_3$) δ 7.53-7.46 (m, 2H), 7.31-7.05 (m, 6H), 3.68-3.59 (m, 2H), 3.57-3.46 (m, 2H), 2.60-2.51 (m, 2H), 1.87-1.82 (m, 2H), 1.65-1.53 (m, 2H), 1.35 (s, 18H), 0.97-0.84 (m, 3H); ESI MS m/z 617 [$C_{32}H_{39}F_3N_4O_5$+H]$^+$.

Preparation of 8-(3-Propyl-phenyl)-8-(4-trifluoromethoxy-phenyl)-2,3,4,8-tetrahydro-imidazo[1,5-a]pyrimidin-6-ylamine A solution of 3 (0.075 g, 0.12 mmol) in 4 M HCl/dioxane (2 mL) was stirred at room temperature for 17 h. The reaction was concentrated and partitioned between methylene chloride (25 mL) and saturated aqueous sodium bicarbonate (25 mL). The organic layer was separated and washed with brine (20 mL), dried over sodium sulfate, filtered and concentrated. Purification by flash chromatography (silica, 97:2.5:0.5 methylene chloride/methanol/concentrated ammonium hydroxide) afforded a colorless oil, 0.055 g (100% yield). The oil was freeze-dried from 2:1 acetonitrile/water (3 mL) to afford the title product as a white solid, 0.035 g, mp 75-79° C.; $^1$H NMR (500 MHz, CD$_3$OD) δ 7.42 (dt, J=8.9, 2.9 Hz, 2H), 7.23-7.19 (m, 3H), 7.14-7.09 (m, 3H), 3.68 (t, J=5.9 Hz, 2H), 3.48-3.46 (m, 2H), 2.54 (t, J=7.4 Hz, 2H), 1.88-1.84 (m, 2H), 1.61-1.56 (m, 2H), 0.90 (t, J=7.3 Hz, 3H); ESI MS m/z 417 [$C_{22}H_{23}F_3N_4O$+H]$^+$.

EXAMPLE 15

Preparation of 3-[6-Amino-8-(4-trifluoromethoxy-phenyl)-2,3,4,8-tetrahydroimidazo[1,5-a]pyrimidin-8-yl]-N-ethyl-benzamide

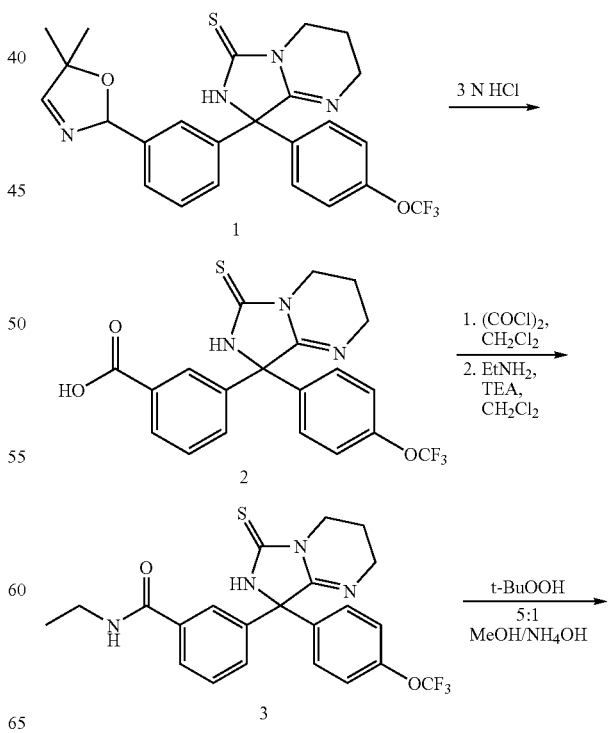

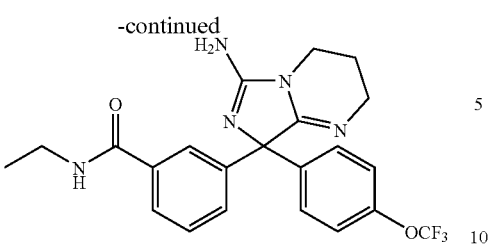

Preparation of Compound 2

A mixture of 1 (0.95 g, 1.94 mmol) and 3 N HCl (25 mL) was heated at reflux for 30 min. After this time, the reaction mixture was cooled to room temperature and concentrated to dryness. To the residue obtained was added 20% aqueous KOH (10 mL) and methanol (10 mL) and the mixture heated at reflux for 30 min. The mixture was then cooled to room temperature, concentrated to remove most of the methanol, acidified with concentrated HCl, and the solid that formed was collected by filtration and dried to afford 2 (0.83 g, 97%) as a white solid: $^1$H NMR (500 MHz, CD$_3$OD) δ 8.11-8.03 (m, 2H), 7.61-7.54 (m, 2H), 7.47-7.44 (m, 2H), 7.39-7.33 (m, 2H), 4.00 (m, 2H), 3.62 (M, 2H), 2.06 (m, 2H); ESI MS m/z 436 [C$_{20}$H$_{16}$F$_3$N$_3$O$_3$S+H]$^+$.

Preparation of Compound 3

Oxalyl chloride (0.12 g, 0.96 mmol) was added to a suspension of 2 (0.20 g, 0.46 mmol) in methylene chloride (3.0 mL). Dimethylformamide (1 drop) was added and the mixture stirred at room temperature for 2 h and then the solvents were removed. The residue was suspended in methylene chloride (3 mL) and diisopropyl ethylamine (0.148 g, 1.15 mmol) was added, followed by ethylamine (0.25 mL of a 2.0 M solution in THF, 0.50 mmol) and the reaction stirred for 2 h. The mixture was diluted with water (30 mL) and methylene chloride (30 mL). The organic layer was separated and washed with 1 N HCl (15 mL), saturated aqueous sodium bicarbonate (15 mL) and brine (15 mL), dried over sodium sulfate, filtered and concentrated. Purification by flash chromatography (silica, ethyl acetate) afforded 3 (0.085 g, 40%) as a white solid: $^1$H NMR (500 MHz, CD$_3$OD) δ 7.81-7.77 (m, 2H), 7.53-7.42 (m, 4H), 7.33-7.27 (m, 2H), 3.95-3.84 (m, 2H), 3.58-3.51 (m, 2H), 3.38 (q, J=7.2 Hz, 2H), 1.97-1.89 (m, 2H), 1.19 (t, J=7.2 Hz, 3H);

Preparation of 3-[6-Amino-8-(4-trifluoromethoxy-phenyl)-2,3,4,8-tetrahydroimidazo[1,5-a]pyrimidin-8-yl]-N-ethyl-benzamide A mixture of 3 (0.085 g, 0.18 mmol) and t-butyl hydroperoxide-(0.49 g of a 70% solution in water, 5.50 mmol) in methanol (10 mL) and concentrated aqueous ammonium hydroxide (2 mL) was stirred overnight at room temperature. After this time, 10% aqueous sodium thiosulfate (2 mL) was added; the mixture concentrated to remove most of the methanol and then the aqueous mixture was extracted with methylene chloride (2×30 mL). The methylene chloride extracts were combined and washed with brine (30 mL), dried over magnesium sulfate, filtered and concentrated. Purification by flash chromatography (silica, 95:5:0.25 methylene chloride/methanol/concentrated ammonium hydroxide) afforded a white solid which was freeze-dried from 1:1 acetonitrile/water (4 mL) to afford the title product as a white solid, 0.041 g (52% yield), mp 129-136° C.; $^1$H NMR (500 MHz, CDCl$_3$) δ 7.88 (t, J=1.7 Hz, 1H), 7.71 (dt, J=6.3, 1.5 Hz, 1H), 7.64 (dt, J=6.6, 1.6 Hz, 1H), 7.48 (d, J=8.9 Hz, 2H), 7.38 (t, J=7.7 Hz, 1H), 7.14 (d, J=8.1 Hz, 2H), 6.36 (br s, 1H), 3.62 (t, J=6.0 Hz, 2H), 3.59 (t, J=5.6 Hz, 2H), 3.49-3.42 (m, 2H), 1.89 (quintet, J=5.8 Hz, 2H), 1.22 (t, J=7.2 Hz, 3H); ESI MS m/z 446 [C$_{22}$H$_{22}$F$_3$N$_5$O$_2$+H]$^+$.

EXAMPLE 16

Preparation of N-{3-[6-Amino-8-(4-trifluoromethoxy-phenyl)-2,3,4,8-tetrahydroimidazo[1,5-a]pyrimidin-8-yl]-phenyl}-propionamide hydrochloride

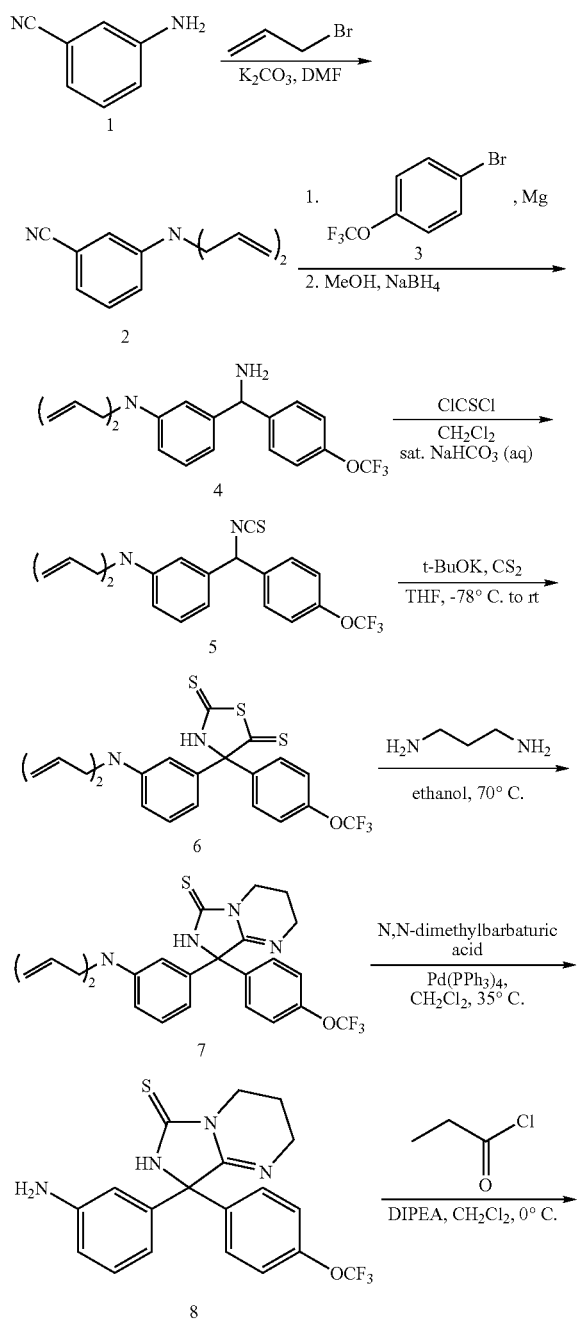

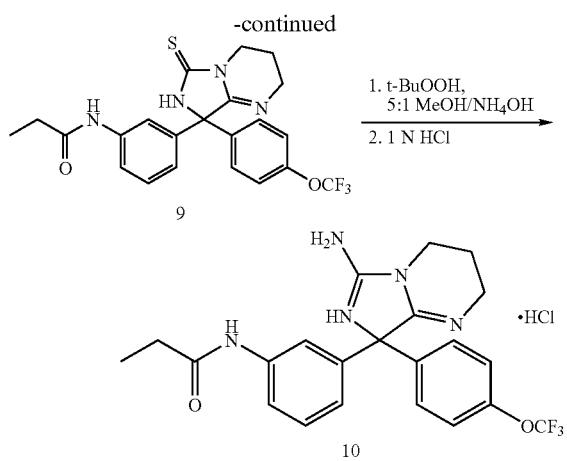

Preparation of Compound 2

A mixture of 1 (3.00 g, 25.4 mmol), allyl bromide (9.22 g, 76.2 mmol), and potassium carbonate (10.5 g, 76.2 mmol) in dimethylformamide (30 mL) was heated at reflux for 18 h. The reaction was then cooled to room temperature, diluted with water (100 mL) and extracted with ethyl acetate (2×150 mL). The organic extracts were combined and washed with brine (3×100 mL), dried over sodium sulfate, filtered and concentrated under reduced pressure. Purification by flash chromatography (silica, 95:5 hexanes/ethyl acetate) afforded 2 (4.10 g, 81%) as a yellow oil: $^1$H NMR (500 MHz, CDCl$_3$) δ 7.23 (m, 1H), 6.92 (d, J=7.4 Hz, 1H), 6.88-6.81 (m, 2H), 5.88-5.76 (m, 2H), 5.23-5.10 (m, 4H), 3.93 (t, J=2.3 Hz, 4H); ESI MS m/z 199 [C$_{13}$H$_{14}$N$_2$+H]$^+$.

Preparation of Compound 4

A mixture of magnesium (0.271 g, 11.3 mmol) and a small crystal of iodine in THF (7 mL) was heated to 50° C. and treated dropwise with a solution of 3 (2.74 g, 11.3 mmol) in THF (15 mL) over a period of 10 min. After stirring at 50° C. for an additional 2 h, the mixture was cooled to room temperature and treated with a solution of 2 (1.50 g, 7.57 mmol) in THF (15 mL). The mixture was then reheated to 65° C. for 2 h. After this time, the reaction was cooled to room temperature then placed in an ice bath and anhydrous methanol (30 mL) was added. After stirring for 30 min at ice bath temperature, sodium borohydride (0.573 g, 15.1 mmol) was added portionwise, the cooling bath was removed and the mixture stirred at room temperature for 2 h. Saturated aqueous ammonium chloride (15 mL) was then added and most of the methanol and THF were removed under reduced pressure. The resulting aqueous mixture was extracted with methylene chloride (2×100 mL), dried over sodium sulfate, filtered and concentrated. Purification by flash chromatography (silica, 1:1 ethyl acetate/hexane) afforded 4 (1.16 g, 42%) as an orange syrup: $^1$H NMR (500 MHz, CDCl$_3$) δ 7.41 (d, J=4.9 Hz, 2H), 7.16-7.10 (m, 3H), 6.67 (s, 1H), 6.64 (d, J=7.5 Hz, 1H), 6.57 (dd, J=5.7, 2.6 Hz, 1H), 5.87-5.75 (m, 2H), 5.15 (t, J=1.7 Hz, 1H), 5.13 (t, J=1.6 Hz, 1H), 5.11 (d, J=2.5 Hz, 3H), 3.89 (d, J=4.8 Hz, 4H), 1.73 (br s, 2H); ESI MS m/z 363 [C$_{20}$H$_{21}$F$_3$N$_2$O+H]$^+$.

Preparation of Compound 5

A mixture of 4 (1.16 g, 3.20 mmol) in methylene chloride (15 mL) and saturated aqueous sodium bicarbonate (15 mL) was cooled with an ice bath, treated with thiophosgene (0.405 g, 3.52 mmol) and stirred vigorously for 1 h. The organic layer was separated, washed with brine (20 mL), dried over sodium sulfate, filtered and concentrated to afford 5 (1.26 g, 98%) as a brown syrup: $^1$H NMR (500 MHz, CDCl$_3$) δ 7.34 (d, J=4.9 Hz, 2H), 7.22-7.14 (m, 3H), 6.63 (d, J=5.8 Hz, 1H), 6.59-6.54 (m, 2H), 5.88 (s, 1H), 5.86-5.77 (m, 2H), 5.18-5.11 (m, 4H), 3.93-3.88 (m, 4H); ESI MS m/z 405 [C$_{21}$H$_{19}$F$_3$N$_2$OS+H]$^+$.

Preparation of Compound 6

To a mixture of potassium t-butoxide (0.38 g, 3.38 mmol) in THF (15 mL) at −78° C. was added dropwise a solution of 5 (1.24 g, 3.07 mmol) and carbon disulfide (0.35 g, 4.61 mmol) in THF (15 mL), over a period of 10 min. The reaction was stirred at −78° C. for 30 min, then warmed to room temperature slowly and stirred for 20 h. The reaction was then concentrated to remove most of the THF and the residue diluted with ethyl acetate (75 mL), water (75 mL) and 1 N HCl (30 mL). The organic layer was separated, washed with brine (30 mL), dried over sodium sulfate, filtered and concentrated to afford 6 (1.58 g, 100%) as a red syrup: $^1$H NMR (300 MHz, CDCl$_3$) δ 7.36 (m, 2H), 7.24-7.06 (m, 3H), 6.74-6.53 (m, 3H), 5.88-5.68 (m, 2H), 5.17-5.06 (m, 4H), 3.95-3.81 (m, 4H); ESI MS m/z 483 [C$_{22}$H$_{19}$F$_3$N$_2$OS$_3$+H]$^+$.

Preparation of Compound 7

A mixture of 6 (1.48 g, 3.08 mmol) and 1,3-diaminopropane (0.68 g, 9.24 mmol) in ethanol (36 mL) was heated at 70° C. for 1.5 h. The reaction was then cooled to room temperature, concentrated and the residue partitioned between ethyl acetate (150 mL) and water (75 mL). The organic layer was separated and washed with brine (75 mL), dried over sodium sulfate, filtered and concentrated. Purification by flash chromatography (silica, 1:3 ethyl acetate/hexanes) afforded 7 (0.622 g, 41%) as a yellow solid: $^1$H NMR (500 MHz, CDCl$_3$) δ 7.41 (d, J=5.0 Hz, 2H), 7.20-7.13 (m, 3H), 7.04 (br s, 1H), 6.64 (dd, J=6.0, 2.4 Hz, 1H), 6.61 (t, J=1.9 Hz, 1H), 6.53 (d, J=6.6 Hz, 1H), 5.83-5.72 (m, 2H), 5.14-5.05 (m, 4H), 3.92-3.81 (m, 6H), 3.63-3.51 (m, 2H), 1.89 (q, J=5.8 Hz, 2H); ESI MS m/z 489 [C$_{25}$H$_{25}$F$_3$N$_4$OS+H]$^+$.

Preparation of Compound 8

A mixture of 7 (0.408 g, 0.84 mmol), N,N-dimethylbarbaturic acid (0.786 g, 5.03 mmol) and tetrakis(triphenylphosphine)palladium(0) (0.019 g, 0.017 mmol) in dichloromethane (2.0 mL) was heated at 35° C. for 3 h. The reaction was then cooled to room temperature, concentrated and the residue partitioned between ether (80 mL) and 10% aqueous sodium carbonate (30 mL). The organic layer separated and washed with 10% aqueous sodium carbonate (30 mL), dried over sodium sulfate, filtered and concentrated. Purification by flash chromatography (silica, 95:5:0.25 methylene chloride/methanol/concentrated ammonium hydroxide) afforded 8 (0.278 g, 82%) as a yellow solid: $^1$H NMR (500 MHz, CDCl$_3$) δ 7.39 (d, J=6.8 Hz, 2H), 7.19-7.09 (m, 4H), 6.67-6.61 (m, 3H), 3.88 (t, J=6.0 Hz, 2H), 3.72 (s, 2H), 3.58 (q, J=6.1 Hz, 2H), 1.89 (q, J=5.5 Hz, 2H); ESI MS m/z 407 [C$_{19}$H$_{17}$F$_3$N$_4$OS+H]$^+$.

Preparation of Compound 9

A mixture of 8 (0.100 g, 0.246 mmol) in dichloromethane (2.0 mL) was cooled to 0° C. and propionyl chloride (0.025 g, 0.270 mmol) and diisopropylethylamine (0.048 g, 0.369 mmol) were added. After stirring at 0° C. for 1 h the reaction was partitioned between dichloromethane (30 mL) and water (20 mL). The organic layer was separated and then washed with 1 N hydrochloric acid (20 mL), saturated aqueous sodium bicarbonate (20 mL), and brine (20 mL), dried over sodium sulfate, filtered and concentrated. Purification by flash chromatography (silica, 1:1 ethyl acetate/hexanes)

afforded 9 (0.044 g, 39%) as a yellow oil: $^1$H NMR (500 MHz, CDCl$_3$) δ 7.70 (d, J=7.5 Hz, 1H), 7.41-7.31 (m, 4H), 7.17 (d, J=7.0 Hz, 4H), 7.04 (d, J=7.4 Hz, 1H), 3.89 (t, J=6.0 Hz, 2H), 3.65-3.54 (m, 2H), 2.36 (q, J=7.5 Hz, 2H), 1.23 (q, J=7.5 Hz, 3H); ESI MS m/z 463 $[C_{22}H_{21}F_3N_4O_2S+H]^+$.

Preparation of N-{3-[6-Amino-8-(4-trifluoromethoxy-phenyl)-2,3,4,8-tetrahydroimidazo[1,5-a]pyrimidin-8-yl]-phenyl}-propionamide hydrochloride A mixture of 8 (0.040 g, 0.086 mmol) and t-butyl hydroperoxide (0.33 g of a 70% solution in water, 2.59 mmol) in methanol (4.0 mL) and concentrated aqueous ammonium hydroxide (1.0 mL) was stirred overnight at room temperature. After this time, 10% aqueous sodium thiosulfate (5 mL) was added; the mixture concentrated to remove most of the methanol and then the aqueous mixture was extracted with methylene chloride (3×20 mL). The methylene chloride extracts were dried over sodium sulfate, filtered and concentrated. Purification by flash chromatography (silica, 95:5:0.25 methylene chloride/methanol/concentrated ammonium hydroxide) afforded 0.017 g of a white solid. This material was then dissolved in 1 N hydrochloric acid (3 mL) and freeze-dried to afford the title product as a white solid, 0.022 g (54% yield), mp 148-150° C.; $^1$H NMR (500 MHz, CD$_3$OD) 7.85 (d, J=1.9 Hz, 1H), 7.50-7.59 (m, 3H), 7.47-7.37 (m, 3H), 7.07 (d, J=5.0 Hz, 1H), 3.91-3.04 (m, 2H), 3.81-3.66 (m, 2H), 2.44-2.34 (m, 2H), 2.19-2.10 (m, 2H), 1.21-1.16 (m, 3H); ESI MS m/z 446 $[C_{22}H_{22}F_3N_5O_2+H]^+$.

EXAMPLE 17

Evaluation of BACE-1 Binding Affinity of Test Compounds

1. Fluorescent Kinetic Assays

Final Assay Conditions: 10 nM human BACE1 (or 10 nM Murine BACE1, 1.5 nM human BACE2), 25 µM substrate (WABC-6, MW 1549.6, from AnaSpec), Buffer: 50 mM Na-Acetate, pH 4.5, 0.05% CHAPS, 25% PBS, room temperature. Na-Acetate was from Aldrich, Cat.# 24,124-5, CHAPS was from Research Organics, Cat. # 1304C 1X, PBS was from Mediatech (Celigro), Cat# 21-031-CV, peptide substrate AbzSEVNLDAEFRDpa was from AnaSpec, Peptide Name: WABC-6

Determination of stock substrate (AbzSEVNLDAEFRDpa) concentration: ~25 mM stock solution is made in DMSO using the peptide weight and MW, and diluted to ~25 µM (1:1000) in 1X PBS. Concentration is determined by absorbance at 354 nm using an extinction coefficient of 18172 $M^{-1}$ $cm^{-1}$, the concentration of stock substrate is corrected, and the substrate stock stored in small aliquots in −80° C.

$$[\text{Substrate Stock}]=ABS^{354\,nm}*10^6/18172 \text{ (in mM)}$$

The extinction coefficient $\epsilon^{354\,nm}$ was adapted from TACE peptide substrate, which had the same quencher-fluorophore pair.

Determination of Stock Enzyme Concentration: the stock concentration of each enzyme is determined by absorbance at 280 nm using an $\epsilon$ of 64150 $M^{-1}$ $cm^{-1}$ for hBACE1 and MuBACE1, 62870 $M^{-1}$ $cm^{-1}$ for hBACE2 in 6 M Guanidinium Hydrochloride (from Research Organics, Cat. # 5134G-2), pH ~6. The extinction coefficient $\epsilon^{280\,nm}$ for each enzyme was calculated based on known amino acid composition and published extinction coefficients for Trp (5.69 $M^{-1}$ $cm^{-1}$) and Tyr (1.28 $M^{-1}$ $cm^{-1}$) residues (Anal. Biochem. 182, 319-326).

Dilution and mixing steps: total reaction volume: 100 µL 2X inhibitor dilutions in buffer A (66.7 mM Na-Acetate, pH 4.5, 0.0667% CHAPS) were prepared, 4X enzyme dilution in buffer A (66.7 mM Na-Acetate, pH 4.5, 0.0667% CHAPS) were prepared, 100 µM substrate dilution in 1X PBS was prepared, and 50 µL 2X Inhibitor, 25 µL 100 µM substrate are added to each well of 96-well plate (from DYNEX Technologies, VWR #: 11311-046), immediately followed by 25 µL 4X enzyme (added to the inhibitor and substrate mix), and the fluorescence readings are initiated.

Fluorescence Readings: Readings at $\lambda_{ex}$ 320 nm and $\lambda_{em}$ 420 nm are taken every 40 sec for 30 min at room temperature and the linear slope for substrate cleavage rate ($v_i$) determined.

Calculation of % Inhibition:

$$\%\text{ Inhibition}=100*(1-v_i/v_0)$$

$v_i$: substrate cleavage rate in the presence of inhibitor $v_0$: substrate cleavage rate in the absence of inhibitor IC$_{50}$ Determination:

$$\%\text{ Inhibition}=((B*IC_{50}^n)+(100*I_0^n))/(IC_{50}^n+I_0^n)$$

(Model # 39 from LSW Tool Bar in Excel, where B is the % inhibition from the enzyme control, which should be close to 0.) % Inhibition is plotted vs. Inhibitor Concentration ($I_0$) and the data fit to the above equation to obtain IC$_{50}$ value and Hill number (n) for each compound. Testing at least 10 different inhibitor concentrations is preferred. Results are presented below in Table I.

TABLE 1

| Example | BACE1 IC$_{50}$, µM |
| --- | --- |
| 1 | 30.0 |
| 2 | 5.3 |
| 3 | 4.7 |
| 4 | 7.1 |
| 5 | 8.2 |
| 6 | 48% at 25 µM |
| 7 | 49% at 25 µM |
| 8 | 0.4 |
| 9 | 0.3 |
| 10 | 1.1 |
| 11 | 38 |
| 12 | 0.21 |
| 13 | 53% at 5 µM |
| 14 | 1.43 |
| 15 | 40% at 0.5 µM |
| 16 | 43% at 2.5 µM |

Results and Discussion

As can be seen from the data shown in Table I, the compounds of the invention are effective inhibitors of BACE1.

What is claimed is:

1. A compound of formula I

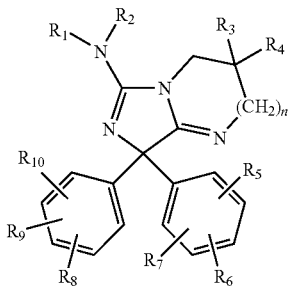

wherein $R_1$ and $R_2$ are each independently H or a $C_1$-$C_4$alkyl group substituted with 0-3 groups selected from halo, nitro, cyano, thiocyanato, cyanato, hydroxyl, alkyl, haloalkyl, alkoxy, haloalkoxy, amino, alkylamino, dialkylamino, formyl, alkoxycarbonyl, carboxyl, alkanoyl, alkylthio, alkylsulphinyl, alkylsulphonyl, carbamoyl, alkylamido, phenyl, phenoxy, benzyl, benzyloxy, heterocyclyl and cycloalkyl;

$R_3$ and $R_4$ are each independently H, or a $C_1$-$C_4$ alkyl group substituted with 0-3 groups selected from halo, nitro, cyano, thiocyanato, cyanato, hydroxyl, alkyl, haloalkyl, alkoxy, haloalkoxy, amino, alkylamino, dialkylamino, formyl, alkoxycarbonyl, carboxyl, alkanoyl, alkylthio, alkylsulphinyl, alkylsulphonyl, carbamoyl, alkylamido, phenyl, phenoxy, benzyl, benzyloxy, heterocyclyl and cycloalkyl; or $R_3$ and $R_4$ may be taken together to form a 4- to 7-membered ring optionally containing one or two heteroatoms selected from O, N or S;

$R_5$, $R_6$ and $R_7$ are each independently H, halogen, $NO_2$, CN, $OR_{11}$, $NR_{12}R_{13}$ or a $C_1$-$C_6$alkyl, $C_1$-$C_6$haloalkyl, $C_2$-$C_6$alkenyl, $C_2$-$C_6$alkynyl, $C_3$-$C_8$cycloalkyl, cycloheteroalkyl, aryl or aryl($C_1$-$C_4$)alkyl group each substituted with 0-3 groups selected from halo, nitro, cyano, thiocyanato, cyanato, hydroxyl, alkyl, haloalkyl, alkoxy, haloalkoxy, amino, alkylamino, dialkylamino, formyl, alkoxycarbonyl, carboxyl, alkanoyl, alkylthio, alkylsulphinyl, alkylsulphonyl, carbamoyl, alkylamido, phenyl, phenoxy, benzyl, benzyloxy, heterocyclyl and cycloalkyl, or when attached to adjacent carbon atoms $R_5$ and $R_6$ may be taken together with the atoms to which they are attached to form a 5- to 7-membered ring optionally containing one or two heteroatoms selected from O, N or S, wherein said 5- to 7-membered ring is substituted with 0-3 groups selected from halo, nitro, cyano, thiocyanato, cyanato, hydroxyl, alkyl, haloalkyl, alkoxy, haloalkoxy, amino, alkylamino, dialkylamino, formyl, alkoxycarbonyl, carboxyl, alkanoyl, alkylthio, alkylsulphinyl, alkylsulphonyl, carbamoyl, alkylamido, phenyl, phenoxy, benzyl, benzyloxy, heterocyclyl and cycloalkyl;

$R_8$, $R_9$ and $R_{10}$ are each independently H, halogen, $NO_2$, CN, $OR_{14}$, $NR_{15}R_{16}$ or a $C_1$-$C_6$alkyl, $C_1$-$C_6$haloalkyl, $C_2$-$C_6$alkenyl, $C_2$-$C_6$alkynyl, $C_3$-$C_8$cycloalkyl, cycloheteroalkyl, aryl or aryl($C_1$-$C_4$)alkyl group each substituted with 0-3 groups selected from halo, nitro, cyano, thiocyanato, cyanato, hydroxyl, alkyl, haloalkyl, alkoxy, haloalkoxy, amino, alkylamino, dialkylamino, formyl, alkoxycarbonyl, carboxyl, alkanoyl, alkylthio, alkylsulphinyl, alkylsulphonyl, carbamoyl, alkylamido, phenyl, phenoxy, benzyl, benzyloxy, heterocyclyl and cycloalkyl; or when attached to adjacent carbon atoms $R_8$ and $R_9$ may be taken together with the atoms to which they are attached to form a 5- to 7-membered ring optionally containing one or two heteroatoms selected from O, N or S, wherein the 5- to 7-membered ring is substituted with 0-3 groups selected from halo, nitro, cyano, thiocyanato, cyanato, hydroxyl, alkyl, haloalkyl, alkoxy, haloalkoxy, amino, alkylamino, dialkylamino, formyl, alkoxycarbonyl, carboxyl, alkanoyl, alkylthio, alkylsulphinyl, alkylsulphonyl, carbamoyl, alkylamido, phenyl, phenoxy, benzyl, benzyloxy, heterocyclyl and cycloalkyl;

n is 1;

$R_{11}$ and $R_{14}$ are each independently H or a $C_1$-$C_6$alkyl, $C_1$-$C_6$haloalkyl, $C_2$-$C_6$alkenyl, $C_2$-$C_6$alkynyl, $C_3$-$C_8$cycloalkyl or aryl group each substituted with 0-3 groups selected from halo, nitro, cyano, thiocyanato, cyanato, hydroxyl, alkyl, haloalkyl, alkoxy, haloalkoxy, amino, alkylamino, dialkylamino, formyl, alkoxycarbonyl, carboxyl, alkanoyl, alkylthio, alkylsulphinyl, alkylsulphonyl, carbamoyl, alkylamido, phenyl, phenoxy, benzyl, benzyloxy, heterocyclyl and cycloalkyl; and $R_{12}$, $R_{13}$, $R_{15}$ and $R_{16}$ are each independently H, $C_1$-$C_4$alkyl, $C_3$-$C_8$cycloalkyl; or $R_{12}$ and $R_{13}$ or $R_{15}$ and $R_{16}$ may be taken together with the atom to which they are attached to form a 5- to 7-membered ring optionally containing an additional heteroatom selected from O, N or S; or a tautomer thereof, a stereoisomer thereof or a pharmaceutically acceptable salt thereof.

2. The compound according to claim 1 wherein $R_1$ and $R_2$ are H.

3. The compound according to claim 1 wherein $R_3$ and $R_4$ are H.

4. The compound according to claim 1 wherein $R_6$, $R_7$, $R_9$ and $R_{10}$ are H.

5. The compound according to claim 1 wherein $R_5$ and $R_8$ are each independently a $C_1$-$C_6$alkyl, $C_1$-$C_6$alkoxy, $C_{1-6}$haloalkyl or benzyl group each substituted with 0-3 groups selected from halo, nitro, cyano, thiocyanato, cyanato, hydroxyl, alkyl, haloalkyl, alkoxy, haloalkoxy, amino, alkylamino, dialkylamino, formyl, alkoxycarbonyl, carboxyl, alkanoyl, alkylthio, alkylsulphinyl, alkylsulphonyl, carbamoyl, alkylamido, phenyl, phenoxy, benzyl, benzyloxy, heterocyclyl and cycloalkyl; and $R_6$, $R_7$, $R_9$ and $R_{10}$ are H.

6. The compound according to claim 1 wherein $R_5$ is $C_1$-$C_6$alkyl, $C_1$-$C_6$alkoxy or $C_{1-6}$haloalkyl.

7. The compound according to claim 1 wherein $R_3$ and $R_4$ are H and $R_5$ is t-butyl, $CF_3$, $C_1$-$C_3$alkoxy or a benzyl group substituted with 0-3 groups selected from halo, nitro, cyano, thiocyanato, cyanato, hydroxyl, alkyl, haloalkyl, alkoxy, haloalkoxy, amino, alkylamino, dialkylamino, formyl, alkoxycarbonyl, carboxyl, alkanoyl, alkylthio, alkylsulphinyl, alkylsulphonyl, carbamoyl, alkylamido, phenyl, phenoxy, benzyl, benzyloxy, heterocyclyl and cycloalkyl.

8. The compound according to claim 7 wherein $R_8$ is H or $C_1$-$C_3$alkoxy; $R_9$ is H or $C_1$-$C_3$alkyl; and $R_6$, $R_7$ and $R_{10}$ are H.

9. The compound according to claim 1 selected from the group consisting of:

8-(4-tert-butylphenyl)-8-phenyl-2,3,4,8-tetrahydroimidazol[1,5-a]pyrimidin-6-amine;

8-(3-benzylphenyl)-8-phenyl-2,3,4,8-tetrahydroimidazol[1,5-a]pyrimidin-6-amine;

8-[3-(4-fluorophenoxy)phenyl]-8-phenyl-2,3,4,8-tetrahydroimidazo[1,5-a]pyrimidin-6-amine;

8-[3-(4-methoxybenzyl)phenyl]-8-phenyl-2,3,4,8-tetrahydroimidazo[1,5-a]pyrimidin-6-amine;
8-[3-(4-fluorobenzyl)phenyl]-8-phenyl-2,3,4,8-tetrahydroimidazo[1,5-a]pyrimidin-6-amine;
8-phenyl-8-[3-(trifluoromethyl)phenyl]-2,3,4,8-tetrahydroimidazo[1,5-a]pyrimidin-6-amine;
8-(3-methoxyphenyl)-8-phenyl-2,3,4,8-tetrahydroimidazo[1,5-a]pyrimidin-6-amine;
8-(4-methoxy-3-methylphenyl)-8-(3-propoxyphenyl)-2,3,4,8-tetrahydroimidazo[1,5-a]pyrimidin-6-amine;
8-(4-methoxy-3-methylphenyl)-3,3-dimethyl-8-(3-propoxyphenyl)-2,3,4,8-tetrahydroimidazo[1,5-a]pyrimidin-6-amine;
8,8-diphenyl-2,3,4,8-tetrahydroimidazo[1,5-α]pyrimidin-6-amine;
8-[3-(2-cyclopropyl-ethyl)-phenyl]-8-(4-trifluoromethoxy-phenyl)-2,3,4,8-tetrahydro-imidazo[1,5-a]pyrimidin-6-ylamine;
8-(3-allylphenyl)-8-(4-trifluoromethoxyphenyl)-2,3,4,8-tetrahydro-imidazo[1,5-a]pyrimidin-6-ylamine;
8-(3-propyl-phenyl)-8-(4-trifluoromethoxy-phenyl)-2,3,4,8-tetrahydro-imidazo[1,5-a]pyrimidin-6-ylamine; or
a tautomer thereof;
a stereoisomer thereof; or
a pharmaceutically acceptable salt thereof.

10. A method for the treatment of a patient suffering from Alzheimer's disease which comprises providing said patient an effective amount of a compound of formula I

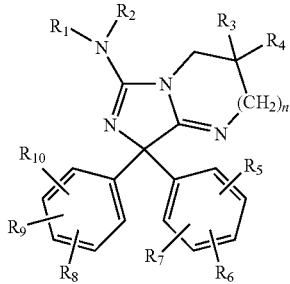

(I)

wherein $R_1$ and $R_2$ are each independently H or a $C_1$-$C_4$alkyl group substituted with 0-3 groups selected from halo, nitro, cyano, thiocyanato, cyanato, hydroxyl, alkyl, haloalkyl, alkoxy, haloalkoxy, amino, alkylamino, dialkylamino, formyl, alkoxycarbonyl, carboxyl, alkanoyl, alkylthio, alkylsulphinyl, alkylsulphonyl, carbamoyl, alkylamido, phenyl, phenoxy, benzyl, benzyloxy, heterocyclyl and cycloalkyl;

$R_3$ and $R_4$ are each independently H, or a $C_1$-$C_4$ alkyl group substituted with 0-3 groups selected from halo, nitro, cyano, thiocyanato, cyanato, hydroxyl, alkyl, haloalkyl, alkoxy, haloalkoxy, amino, alkylamino, dialkylamino, formyl, alkoxycarbonyl, carboxyl, alkanoyl, alkylthio, alkylsulphinyl, alkylsulphonyl, carbamoyl, alkylamido, phenyl, phenoxy, benzyl, benzyloxy, heterocyclyl and cycloalkyl; or $R_3$ and $R_4$ may be taken together to form a 4- to 7-membered ring optionally containing one or two heteroatoms selected from O, N or S;

$R_5$, $R_6$ and $R_7$ are each independently H, halogen, $NO_2$, CN, $OR_{11}$, $NR_{12}R_{13}$ or a $C_1$-$C_6$alkyl, $C_1$-$C_6$haloalkyl, $C_2$-$C_6$alkenyl, $C_2$-$C_6$alkynyl, $C_3$-$C_8$cycloalkyl, cycloheteroalkyl, aryl or aryl($C_1$-$C_4$)alkyl group each substituted with 0-3 groups selected from halo, nitro, cyano, thiocyanato, cyanato, hydroxyl, alkyl, haloalkyl, alkoxy, haloalkoxy, amino, alkylamino, dialkylamino, formyl, alkoxycarbonyl, carboxyl, alkanoyl, alkylthio, alkylsulphinyl, alkylsulphonyl, carbamoyl, alkylamido, phenyl, phenoxy, benzyl, benzyloxy, heterocyclyl and cycloalkyl; or when attached to adjacent carbon atoms $R_5$ and $R_6$ may be taken together with the atoms to which they are attached to form a 5- to 7-membered ring optionally containing one or two heteroatoms selected from O, N or S, wherein said 5- to 7-membered ring is substituted with 0-3 groups selected from halo, nitro, cyano, thiocyanato, cyanato, hydroxyl, alkyl, haloalkyl, alkoxy, haloalkoxy, amino, alkylamino, dialkylamino, formyl, alkoxycarbonyl, carboxyl, alkanoyl, alkylthio, alkylsulphinyl, alkylsulphonyl, carbamoyl, alkylamido, phenyl, phenoxy, benzyl, benzyloxy, heterocyclyl and cycloalkyl;

$R_8$, $R_9$ and $R_{10}$ are each independently H, halogen, $NO_2$, CN, $OR_{14}$, $NR_{15}R_{16}$ or a $C_1$-$C_6$alkyl, $C_1$-$C_6$haloalkyl, $C_2$-$C_6$alkenyl, $C_2$-$C_6$alkynyl, $C_3$-$C_8$cycloalkyl, cycloheteroalkyl, aryl or aryl($C_1$-$C_4$)alkyl group each substituted with 0-3 groups selected from halo, nitro, cyano, thiocyanato, cyanato, hydroxyl, alkyl, haloalkyl, alkoxy, haloalkoxy, amino, alkylamino, dialkylamino, formyl, alkoxycarbonyl, carboxyl, alkanoyl, alkylthio, alkylsulphinyl, alkylsulphonyl, carbamoyl, alkylamido, phenyl, phenoxy, benzyl, benzyloxy, heterocyclyl and cycloalkyl; or when attached to adjacent carbon atoms $R_8$ and $R_9$ may be taken together with the atoms to which they are attached to form a 5- to 7-membered ring optionally containing one or two heteroatoms selected from O, N or S, wherein the 5- to 7-membered ring is substituted with 0-3 groups selected from halo, nitro, cyano, thiocyanato, cyanato, hydroxyl, alkyl, haloalkyl, alkoxy, haloalkoxy, amino, alkylamino, dialkylamino, formyl, alkoxycarbonyl, carboxyl, alkanoyl, alkylthio, alkylsulphinyl, alkylsulphonyl, carbamoyl, alkylamido, phenyl, phenoxy, benzyl, benzyloxy, heterocyclyl and cycloalkyl;

n is 1;

$R_{11}$ and $R_{14}$ are each independently H or a $C_1$-$C_6$alkyl, $C_1$-$C_6$haloalkyl, $C_2$-$C_6$alkenyl, $C_2$-$C_6$alkynyl, $C_3$-$C_8$cycloalkyl or aryl group each substituted with 0-3 groups selected from halo, nitro, cyano, thiocyanato, cyanato, hydroxyl, alkyl, haloalkyl, alkoxy, haloalkoxy, amino, alkylamino, dialkylamino, formyl, alkoxycarbonyl, carboxyl, alkanoyl, alkylthio, alkylsulphinyl, alkylsulphonyl, carbamoyl, alkylamido, phenyl, phenoxy, benzyl, benzyloxy, heterocyclyl and cycloalkyl; and $R_{12}$, $R_{13}$, $R_{15}$ and $R_{16}$ are each independently H, $C_1$-$C_4$alkyl, $C_3$-$C_8$cycloalkyl; or $R_{12}$ and $R_{13}$ or $R_{15}$ and $R_{16}$ may be taken together with the atom to which they are attached to form a 5- to 7-membered ring optionally containing an additional heteroatom selected from O, N or S; or a tautomer thereof, a stereoisomer thereof or a pharmaceutically acceptable salt thereof.

11. A pharmaceutical composition which comprises a pharmaceutical acceptable carrier and an effective amount of a compound of formula (I)

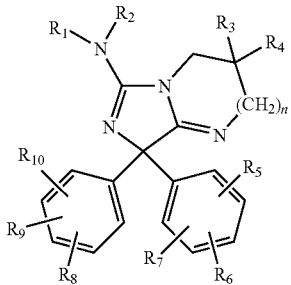

(I)

wherein $R_1$ and $R_2$ are each independently H or a $C_1$-$C_4$alkyl group substituted with 0-3 groups selected from halo, nitro, cyano, thiocyanato, cyanato, hydroxyl, alkyl, haloalkyl, alkoxy, haloalkoxy, amino, alkylamino, dialkylamino, formyl, alkoxycarbonyl, carboxyl, alkanoyl, alkylthio, alkylsulphinyl, alkylsulphonyl, carbamoyl, alkylamido, phenyl, phenoxy, benzyl, benzyloxy, heterocyclyl and cycloalkyl;

$R_3$ and $R_4$ are each independently H, or a $C_1$-$C_4$ alkyl group substituted with 0-3 groups selected from halo, nitro, cyano, thiocyanato, cyanato, hydroxyl, alkyl, haloalkyl, alkoxy, haloalkoxy, amino, alkylamino, dialkylamino, formyl, alkoxycarbonyl, carboxyl, alkanoyl, alkylthio, alkylsulphinyl, alkylsulphonyl, carbamoyl, alkylamido, phenyl, phenoxy, benzyl, benzyloxy, heterocyclyl and cycloalkyl, or $R_3$ and $R_4$ may be taken together to form a 4- to 7-membered ring optionally containing one or two heteroatoms selected from O, N or S;

$R_5$, $R_6$ and $R_7$ are each independently H, halogen, $NO_2$, CN, $OR_{11}$, $NR_{12}R_{13}$ or a $C_1$-$C_6$alkyl, $C_1$-$C_6$haloalkyl, $C_2$-$C_6$alkenyl, $C_2$-$C_6$alkynyl, $C_3$-$C_8$cycloalkyl, cycloheteroalkyl, aryl or aryl($C_1$-$C_4$)alkyl group each substituted with 0-3 groups selected from halo, nitro, cyano, thiocyanato, cyanato, hydroxyl, alkyl, haloalkyl, alkoxy, haloalkoxy, amino, alkylamino, dialkylamino, formyl, alkoxycarbonyl, carboxyl, alkanoyl, alkylthio, alkylsulphinyl, alkylsulphonyl, carbamoyl, alkylamido, phenyl, phenoxy, benzyl, benzyloxy, heterocyclyl and cycloalkyl; or when attached to adjacent carbon atoms $R_5$ and $R_6$ may be taken together with the atoms to which they are attached to form a 5- to 7-membered ring optionally containing one or two heteroatoms selected from O, N or S, wherein said 5- to 7-membered ring is substituted with 0-3 groups selected from halo, nitro, cyano, thiocyanato, cyanato, hydroxyl, alkyl, haloalkyl, alkoxy, haloalkoxy, amino, alkylamino, dialkylamino, formyl, alkoxycarbonyl, carboxyl, alkanoyl, alkylthio, alkylsulphinyl, alkylsulphonyl, carbamoyl, alkylamido, phenyl, phenoxy, benzyl, benzyloxy, heterocyclyl and cycloalkyl;

$R_8$, $R_9$ and $R_{10}$ are each independently H, halogen, $NO_2$, CN, $OR_{14}$, $NR_{15}R_{16}$ or a $C_1$-$C_6$alkyl, $C_1$-$C_6$haloalkyl, $C_2$-$C_6$alkenyl, $C_2$-$C_6$alkynyl, $C_3$-$C_8$cycloalkyl, cycloheteroalkyl, aryl or aryl($C_1$-$C_4$)alkyl group each substituted with 0-3 groups selected from halo, nitro, cyano, thiocyanato, cyanato, hydroxyl, alkyl, haloalkyl, alkoxy, haloalkoxy, amino, alkylamino, dialkylamino, formyl, alkoxycarbonyl, carboxyl, alkanoyl, alkylthio, alkylsulphinyl, alkylsulphonyl, carbamoyl, alkylamido, phenyl, phenoxy, benzyl, benzyloxy, heterocyclyl and cycloalkyl; or when attached to adjacent carbon atoms $R_8$ and $R_9$ may be taken together with the atoms to which they are attached to form a 5- to 7-membered ring optionally containing one or two heteroatoms selected from O, N or S, wherein the 5- to 7-membered ring is substituted with 0-3 groups selected from halo, nitro, cyano, thiocyanato, cyanato, hydroxyl, alkyl, haloalkyl, alkoxy, haloalkoxy, amino, alkylamino, dialkylamino, formyl, alkoxycarbonyl, carboxyl, alkanoyl, alkylthio, alkylsulphinyl, alkylsulphonyl, carbamoyl, alkylamido, phenyl, phenoxy, benzyl, benzyloxy, heterocyclyl and cycloalkyl;

n is 1;

$R_{11}$ and $R_{14}$ are each independently H or a $C_1$-$C_6$alkyl, $C_1$-$C_6$haloalkyl, $C_2$-$C_6$alkenyl, $C_2$-$C_6$alkynyl, $C_3$-$C_8$cycloalkyl or aryl group each substituted with 0-3 groups selected from halo, nitro, cyano, thiocyanato, cyanato, hydroxyl, alkyl, haloalkyl, alkoxy, haloalkoxy, amino, alkylamino, dialkylamino, formyl, alkoxycarbonyl, carboxyl, alkanoyl, alkylthio, alkylsulphinyl, alkylsulphonyl, carbamoyl, alkylamido, phenyl, phenoxy, benzyl, benzyloxy, heterocyclyl and cycloalkyl; and $R_{12}$, $R_{13}$, $R_{15}$ and $R_{16}$ are each independently H, $C_1$-$C_4$alkyl, $C_3$-$C_8$cycloalkyl; or $R_{12}$ and $R_{13}$ or $R_{15}$ and $R_{16}$ may be taken together with the atom to which they are attached to form a 5- to 7-membered ring optionally containing an additional heteroatom selected from O, N or S; or a tautomer thereof, a stereoisomer thereof or a pharmaceutically acceptable salt thereof.

12. The pharmaceutical composition according to claim 11 having a compound of formula I wherein $R_1$ and $R_2$ are H.

13. The pharmaceutical composition according to claim 12 having a compound of formula I wherein $R_3$ and $R_4$ are H.

14. The pharmaceutical composition according to claim 13 having a compound of formula I wherein $R_3$, $R_4$, $R_6$, $R_7$ and $R_{10}$ are H and $R_5$ is t-butyl, $CF_3$, $C_1$-$C_3$alkoxy or a benzyl group substituted with 0-3 groups selected from halo, nitro, cyano, thiocyanato, cyanato, hydroxyl, alkyl, haloalkyl, alkoxy, haloalkoxy, amino, alkylamino, dialkylamino, formyl, alkoxycarbonyl, carboxyl, alkanoyl, alkylthio, alkylsulphinyl, alkylsulphonyl, carbamoyl, alkylamido, phenyl, phenoxy, benzyl, benzyloxy, heterocyclyl and cycloalkyl.

15. The pharmaceutical composition according to claim 14 having a compound of formula I wherein $R_8$ is H or $C_1$-$C_3$alkoxy and $R_9$ is H or $C_1$-$C_3$alkyl.

16. The pharmaceutical composition according to claim 11 having a compound of formula I selected from the group consisting of:
  8-(4-tert-butylphenyl)-8-phenyl-2,3,4,8-tetrahydroimidazol[1, 5-a]pyrimidin-6-amine;
  8-(3-benzylphenyl)-8-phenyl-2,3,4,8-tetrahydroimidazol[1,5-a]pyrimidin-6-amine;
  8-[3-(4-fluorophenoxy)phenyl]-8-phenyl-2,3,4,8-tetrahydroimidazo[1,5-a]pyrimidin-6-amine;
  8-[3-(4-methoxybenzyl)phenyl]-8-phenyl-2,3,4,8-tetrahydroimidazo[1,5-a]pyrimidin-6-amine;
  8-[3-(4-fluorobenzyl)phenyl]-8-phenyl-2,3,4,8-tetrahydroimidazo[1,5-a]pyrimidin-6-amine;
  8-phenyl-8-[3-(trifluoromethyl)phenyl]-2,3,4,8-tetrahydroimidazo[1,5-a]pyrimidin-6-amine;
  8-(3-methoxyphenyl)-8-phenyl-2,3,4,8-tetrahydroimidazo[1,5-a]pyrimidin-6-amine;
  8-(4-methoxy-3-methylphenyl)-8-(3-propoxyphenyl)-2,3,4,8-tetrahydroimidazo[1,5-a]pyrimidin-6-amine;
  8-(4-methoxy-3-methylphenyl)-3,3-dimethyl-8-(3-propoxyphenyl)-2,3,4,8-tetrahydroimidazo[1,5-a]pyrimidin-6-amine;

8,8-diphenyl-2,3,4,8-tetrahydroimidazo[1,5-α]pyrimidin-6-amine;

8-[3-(2-cyclopropyl-ethyl)-phenyl]-8-(4-trifluoromethoxy-phenyl)-2,3,4,8-tetrahydro-imidazo[1,5-a]pyrimidin-6-ylamine;

8-(3-allylphenyl)-8-(4-trifluoromethoxyphenyl)-2,3,4,8-tetrahydro-imidazo[1,5-a]pyrimidin-6-ylamine;

8-(3-propyl-pheny)-8-(4-trifluoromethoxy-pheny)-2,3,4,8-tetrahydro-imidazo[1,5-a]pyrimidin-6-ylamine; or a tautomer thereof;

a stereoisomer thereof; or a pharmaceutically acceptable salt thereof.

* * * * *